(12) United States Patent
Ayadat

(10) Patent No.: US 11,215,549 B2
(45) Date of Patent: *Jan. 4, 2022

(54) HYDRAULIC CONFINEMENT AND MEASURING SYSTEM FOR DETERMINING HYDRAULIC CONDUCTIVITY OF POROUS CARBONATES AND SANDSTONES

(71) Applicant: Prince Mohammad Bin Fahd University, Dhahran (SA)

(72) Inventor: Tahar Ayadat, Dhahran (SA)

(73) Assignee: Prince Mohammad Bin Fahd University, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/022,405

(22) Filed: Sep. 16, 2020

(65) Prior Publication Data
US 2021/0381946 A1     Dec. 9, 2021

Related U.S. Application Data

(63) Continuation of application No. 16/892,790, filed on Jun. 4, 2020, now Pat. No. 10,809,175.

(51) Int. Cl.
*G01N 15/08*     (2006.01)
*G01N 33/24*     (2006.01)

(52) U.S. Cl.
CPC ..... *G01N 15/0826* (2013.01); *G01N 15/0806* (2013.01); *G01N 33/24* (2013.01)

(58) Field of Classification Search
CPC ........... G01N 15/0826; G01N 15/0806; G01N 33/24; B01F 7/00033; B01F 7/00141;
(Continued)

(56) References Cited

U.S. PATENT DOCUMENTS 3,638,478 A * 2/1972 Dietert .................. G01N 3/10
                                                        73/73
6,655,192 B2    12/2003 Chavdar
(Continued)

FOREIGN PATENT DOCUMENTS

CN          3923954 B2    6/2007
CN        101865811 A    10/2010
(Continued)

OTHER PUBLICATIONS

S.G. Goh, et al., "Modification of triaxial apparatus for permeability measurement of unsaturated soils", Soils and Foundations, vol. 55, No. 1, 2015, pp. 63-73.

*Primary Examiner* — Suman K Nath
(74) *Attorney, Agent, or Firm* — Oblon, McClelland, Maier & Neustadt, L.L.P.

(57) ABSTRACT

A permeameter apparatus and method of measuring hydraulic permeability of porous samples, that includes multiple tube manometers stacked vertically at equal intervals on the same side wall of a compression cell containing the sample. The levels of the water menisci in the stacked manometers characterize the temporal and spatial profile of hydraulic conductivity, which can be measured in the constant and falling head regimes in the same apparatus. The apparatus is enabled with a sample compression system imitating the geostatic pressure profiles at different depths of the sample extraction. The apparatus and method allow measurement of time-dependent hydraulic conductivity in anisotropic media at variable pressures.

6 Claims, 14 Drawing Sheets

(58) Field of Classification Search
CPC .............. B01F 7/00175; B01F 7/00425; B01F 7/00291; B01F 2215/0422; B01F 2215/0431
See application file for complete search history.

(56) References Cited

U.S. PATENT DOCUMENTS

2019/0033198 A1* 1/2019 Atapour .............. G01N 15/082
2020/0132584 A1  4/2020 Hollander

FOREIGN PATENT DOCUMENTS

CN  101813606 B  4/2011
CN  101915718 B  1/2012

* cited by examiner

Coring Soft Material
(Inner tube extended)

Coring Harder Material
(Inner tube retracted)

HYDRAULIC CONFINEMENT AND MEASURING SYSTEM FOR DETERMINING HYDRAULIC CONDUCTIVITY OF POROUS CARBONATES AND SANDSTONES

CROSS REFERENCE TO RELATED APPLICATIONS

The present application is a continuation of U.S. application Ser. No. 16/892,790, allowed, having a filing date of Jun. 4, 2020.

BACKGROUND

Technical Field

The invention relates to a device and method of soil hydraulic permeability measurement.

Description of the Related Art

In the design of geotechnical engineering projects, one of the most important soil properties of interest to the soil engineer is permeability. To some degree, permeability plays a role in the design of almost any structure. The properties that are related to soil permeability include durability of concrete, seepage through earth dams and embankments of canals, seepage under sheet pile walls, the rate of settlement, methods for lowering the groundwater table during construction, pre-wetting and ponding, etc.

Groundwater contamination is a growing concern in the agricultural and waste management industry. Seepage losses from animal-waste storages, municipal lagoons, and industrial waste retention ponds including mine tailings retention ponds, are common sources of groundwater pollution. A livestock operation produces large amounts of organic effluent that are often stored on site. Typically, the most feasible and cost-effective method to store and/or treat organic waste is to contain the waste in a lagoon or retention pond. The bottom of these lagoons is generally made from a semi-impermeable layer comprised of synthetic or clayey soil material. In most cases, the cost of synthetic impermeable liners is greater than compacted clay liners, and therefore clay liners are used more often for agricultural waste management applications.

A main concern relating to clay liners is their ability to properly maintain a relatively impermeable barrier between the waste and the surrounding material over time without seepage flows that could impact groundwater quality in the area. When manure storage lagoons require maintenance or are emptied for organic fertilizing purposes, they are usually agitated to mix the solids that have settled out. This agitation process can loosen and partially remove the upper layer of the saturated clay liner, which inevitably causes deterioration in the liner thickness and results in less desirable hydraulic conductivity. The guidelines given by the United States Environmental Protection Agency (EPA) for the thickness of a clay liner is one meter with a hydraulic conductivity (K), of not greater than $1 \times 10^{-7}$ cm/s. Accurate estimates of hydraulic conductivity are an important tool for monitoring existing sites.

Many geotechnical and environmental problems involving unsaturated soils require an understanding of the unsaturated permeability of the soils. These problems include the study of stability of slopes, road and railway embankments, earth dams, clay barriers for the containment of contaminated soils, water management structures, contaminant transport in unsaturated soil zones and many more. The permeability of soil is a soil property which describes the rate of water flow through the soil. The permeability of saturated soil, with respect to the water phase, is a function of the void ratio of the soil. However, in unsaturated soil, the permeability of the soil, with respect to the water phase, is a function of both the void ratio and the water content of the soil.

For the case of collapsible soils, which are defined as any unsaturated soil that goes through a radical rearrangement of particles and a large loss of volume upon wetting with or without additional loading, the coefficient of permeability is not constant and change with time. For this type of soils, the coefficient of permeability changes with the volume change of soils upon wetting (i.e. volume decrease or vertical strain). Therefore, the coefficient of permeability of these soils cannot be measured by conventional testing equipment. At the beginning of the test and during the saturation process of a collapsible soil specimen, the soil inside the permeability cell collapses, leading to a radical rearrangement of particles and a large volume decrease. The value of the coefficient of permeability calculated represents the permeability of the soil at its final stage (i.e. the coefficient of permeability of the soil after collapsing). In many conceivable situations, there is a need to measure the variation of the coefficient of permeability of a collapsible soil with time or with vertical strain change.

There are approaches addressing soil permeability measurements. Two of the most common methods of determining hydraulic conductivity in the laboratory are Constant Head and Falling Head methods. The constant head permeameter method delivers a constant supply of fluid to a porous medium to maintain a given pressure head. The hydraulic conductivity is specified by the relationship:

$$K = \frac{LQ}{H\pi R^2} \qquad (1)$$

where

Q—is the volume flow rate defined by the cross-sectional area of the tube multiplied by the velocity of the fluid [m3/sec];

L—is the length of the trajectory [m];

$\pi R^2$—is the cross-section in the assumption of being circular [m2];

H—is the hydrostatic pressure (or head), measured in N/m2 (newtons per square meter).

The resulting constant K is the ratio of the Darcy permeability (D, m2) and dynamic viscosity (N×sec/m$^2$).

$$K = D/\mu \qquad (2)$$

In more complex and dynamic situations (as is the case for most water migration problems through soil), equations (1)-(2) are first written in the differential form and are integrated according to the groundwater flow equation.

A mass balance must be performed, and used along with Darcy's law, to arrive at a transient groundwater flow equation. This balance is analogous to the energy balance used in heat transfer to arrive at the heat equation. It is simply a statement of accounting, that for a given control volume, aside from sources or sinks, mass cannot be created or destroyed. The conservation of mass states that, for a given increment of time (Δt), the difference between the mass flowing in across the boundaries ($M_{in}$), the mass flowing out across the boundaries ($M_{out}$), and the generating sources within the volume ($M_{gen}$), is the change in storage.

$$\frac{Mstor}{dt} = \frac{Min}{dt} - \frac{Mout}{dt} + \frac{Mgen}{dt} \quad (3)$$

Mass can be represented as density times volume, and under most conditions, water can be considered incompressible (density does not depend on pressure). The mass fluxes across the boundaries then become volume fluxes (as are found in Darcy's law). Using Taylor series to represent the in and out flux terms across the boundaries of the control volume, and using the divergence theorem to turn the flux across the boundary into a flux over the entire volume, the final form of the groundwater flow equation (in the differential form) is:

$$Ss \frac{dh}{dt} = -\nabla g - G \quad (4)$$

Where $S_s$ is the specific storage, defined as the capacity of the unit to accept the accumulating fluid.

This mathematical statement indicates that the change in hydraulic head with time (left-hand side) equals the negative divergence of the flux through the control volume (q) and the source terms (G) in the control volume. This equation has both head (pressure) and flux as unknowns, but Darcy's law relates flux to hydraulic heads, so substituting it in for the flux (q) leads to:

$$Ss \frac{dh}{dt} = -\nabla(-K\nabla h) - G \quad (5)$$

Now if hydraulic conductivity (K) is spatially uniform and isotropic (rather than a tensor), it can be taken out of the spatial derivative, simplifying them to the Laplacian, this makes the equation:

$$Ss \frac{dh}{dt} = -K\nabla 2h) - G \quad (6)$$

Dividing through by the specific storage (Ss), puts hydraulic diffusivity (α=K/Ss or equivalently, α=T/S) on the right-hand side. The hydraulic diffusivity is proportional to the speed at which a finite pressure pulse propagates through the system (large values of α lead to fast propagation of signals). The groundwater flow equation then becomes:

$$\frac{dh}{dt} = -a\nabla 2h - G \quad (7)$$

Where the sink/source term, G, now has the same units but is divided by the appropriate storage term (as defined by the hydraulic diffusivity substitution).

Equation (7) can be further simplified to improve its solvability and usability. In rectangular 3D coordinates, the general Laplacian operator in (7) becomes (for three-dimensional flow) specifically:

$$\frac{dh}{dt} = -a\left[\frac{\partial 2h}{\partial x2} + \frac{\partial 2h}{\partial y2} + \frac{\partial 2h}{\partial z2}\right] - G \quad (8)$$

For stationary conditions, both dh/dt and G become zero, and equation (8) becomes a solvable Laplace equation:

$$0 = -a\left[\frac{\partial 2h}{\partial x2} + \frac{\partial 2h}{\partial y2} + \frac{\partial 2h}{\partial z2}\right] \quad (9)$$

For non-stationary conditions, but when fluid flows through a narrow vertical channel:

$$\frac{dh}{dt} = -a\left[\frac{\partial 2h}{\partial z2}\right] - G \quad (10)$$

Equation (10) can be solved numerically or graphically, assuming a linear gradient of (dh/dz) as a function of z-coordinate with the simultaneous measurement of (dh/dt) parameter. The coefficients a and G can be also found by fitting the experimental data to the form (10).

Devices for measuring soil permeability are known. However, conventional measuring devices are not suitable for constant hydrostatic head regimes while addressing non-stationary flows in freshly percolated unsaturated granular and/or swellable media.

CN101915718B titled "Consolidation and permeability test device of multifunctional soil and test method thereof" utilizes a loading system, a pressure chamber, a data acquisition system, and a water reservoir. The system is suitable for measuring dynamic regimes. However, the dynamic loading systems is applied in contrast to the fixed constant hydrostatic head, which is more difficult to interpret analytically as compared with equation (10).

JP03923954B2 titled "Consolidation permeability test apparatus and test method"—utilizes a loading system, a permeability cell, and a measure of permeability using water. The system utilizes a pressure source to apply pressure via a pressure pipe, which makes it less suitable for description by equation (10).

CN101813606B titled "Test method for determining saturated/unsaturated permeability of soil" utilizes a pressure chamber which is, a vertical stress loading process, a suction balance and a water flow rate measuring process. However, the prior art does not describe using of static hydrostatic head production as an approach to address dynamic soil permeability situations, such as swellable soils, wettability, structural changes upon moisturizing, structural changes upon compression as they develop.

CN101865811A titled "Measurement method for soil seepage parameters under three-way stress loading" describes using a pressure chamber, a three-way stress loading system, and a liquid level measuring tube. The system uses a first water volume measuring tube and a second water volume measuring tube. The publication does not describe the use of manometers or a data acquisition system to inform the parameters of equation (10).

U.S. Pat. No. 6,655,192B2 titled "Permeameter-Porosimeter—Chavdar" discloses a device to measure permeability and porosity of porous materials in normal and lateral directions. The system is not specifically used for measuring the permeability of soil but describes a loading process and a displacement measuring process. A static loading system to assess non-stationary regimes is not described.

The publication by Goh S G, Rahardjo H, Leong E C. titled "Modification of triaxial apparatus for permeability measurement of unsaturated soils". Soils and Foundations. 2015 Feb. 1; 55(1):63-73, describes an equipment setup that allows permeability tests and shear strength tests of unsaturated soils to be conducted using one soil specimen where multiple cycles of drying and wetting is performed. Goh et al. do not describe the use of static load for measuring dynamic permeability.

Many devices are available on the market that utilize static loads and wall manometers to measure the pressure loss related to a volume flow of water through a soil sample. The manometers for granular soils permeability measurement are manufactured by Gilson INC., Humboldt Mfg., Karol-Warner. These constant head permeameter are most suitable for estimating the hydraulic conductivity of coarse sands and gravels because of the high permeability of these materials, while the falling head permeameter is more appropriate for fine silt and clay-like soils (See: Wanielista, Martin, Robert Kersten, and Ron Eaglin. Hydrology: Water quantity and quality control. John Wiley and Sons, 1997).

Even with the existing variety of hydraulic soil permeation measurement techniques, an absence of a reliable analytical method precludes achieving reliable permeability characterization and predicting for the unsaturated soils. Accordingly, the present disclosure provides a simple device and a method that use provides non-stationary permeability analysis of diverse porous media, including unsaturated soils.

SUMMARY OF THE INVENTION

According to a first aspect, the invention discloses a device for measuring water permeability in unsaturated soils.

According to a second aspect, the device comprises stacked manometers on a side wall which provide the time- and position-dependent trends of hydrostatic head loss, allowing to derive time-dependent permeability values.

According to a third aspect, the device comprises a loading or compression system, which imitates the geostatic pressure at a depth of the sample core extraction and allows to model the spatial, temporal and directional distribution of hydraulic conductivity.

According to a fourth aspect, the device uses the soil cores extracted by directional drilling in vertical and slanted directions.

According to a fifth aspect, the permeability metric is non-stationary and follows soil's structural re-arrangement upon moisturizing.

According to a sixth aspect, the device relies on a stationary (constant) source of hydraulic pressure created by a constant height of water column.

According to a seventh aspect, the device is accompanied by a data processing system incorporating a controller, analyzing the distribution of hydrostatic pressure as a function of height and of time, flow volume rate [m³/sec] in and out of the testing cell as a function of time, temperature, compression and deformation of the specimen.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
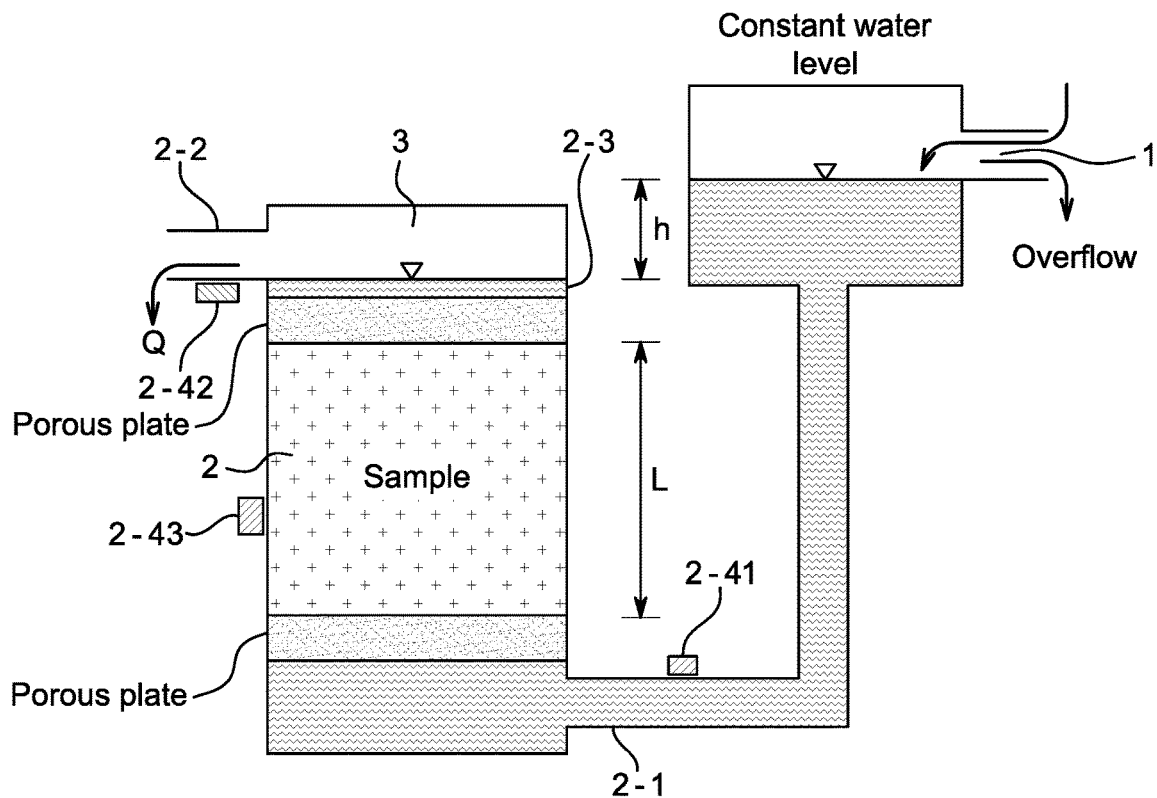
FIG. 1: Constant head design of a soil permeability experiment.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Additionally, within the description of this disclosure, where a numerical limit or range is stated, the endpoints are included unless stated otherwise. Also, all values and subranges within a numerical limit or range are specifically included as if explicitly written out.

As used herein, the term "hydraulic conductivity", symbolically represented as K, is a property of soils and rocks that describes the ease with which a fluid (usually water) can move through pore spaces or fractures. It depends on the intrinsic permeability of the material, the degree of saturation, and on the density and viscosity of the fluid. Saturated hydraulic conductivity, Ksat, describes water movement through saturated media. By definition, hydraulic conductivity is the ratio of velocity to hydraulic gradient indicating permeability of porous media.

As used herein, the term "an aquifer test (or a pumping test)" is conducted to evaluate an aquifer by "stimulating" the aquifer through constant pumping and observing the aquifer's "response" (drawdown) in observation wells. Aquifer testing is a common tool that hydrogeologists use to characterize a system of aquifers, aquitards and flow system boundaries.

As used herein, the term "slug test" is a particular type of aquifer test where water is quickly added or removed from groundwater well, and the change hydraulic head is monitored through time, to determine the near-well aquifer characteristics. It is a method used by hydrogeologists and civil engineers to determine the transmissivity/hydraulic conductivity and storativity of the material the well is completed in.

As used herein, the term "storativity" or the storage coefficient is the volume of water released from storage per unit decline in hydraulic head in the aquifer, per unit area of the aquifer. Storativity is a dimensionless quantity and is always greater than 0.

As used herein, the term "infiltration" is the process by which water on the ground surface enters the soil. It is commonly used in both hydrology and soil sciences. The infiltration capacity is defined as the maximum rate of infiltration. It is most often measured in meters per day but can also be measured in other units of distance over time if necessary. The infiltration capacity decreases as the soil moisture content of soils surface layers increases. If the precipitation rate exceeds the infiltration rate, a runoff will usually occur unless there is some physical barrier.

As used herein, the term "confined aquifer" indicates a water-carrying layer bracketed from the top and bottom by water-impermeable layers.

As used herein, the term "unconfined aquifer" indicates a water-carrying layer limited by a water-impermeable layer on one side only.

Apparatus and Method

Figure 2:
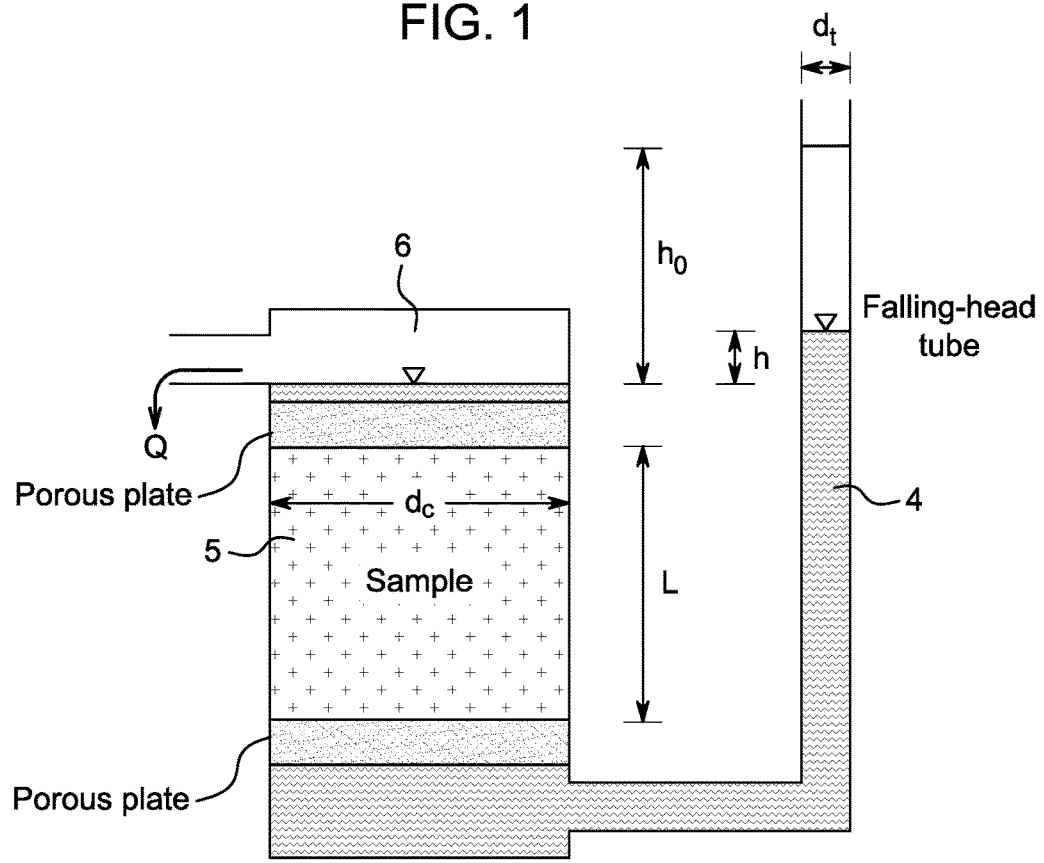
FIG. 2: Declining head design of a soil permeability experiment.

FIGS. 1 and 2 present the general scheme of the soil permeability experiments. The constant head permeameter method delivers a constant supply of fluid to a porous medium to maintain a given pressure head (FIG. 1). The inflow of water 1 percolates the porous sample 2 from below and exists through the duct 3. Alternatively, the falling head permeameter (FIG. 2) uses a time-dependent profile of hydrostatic pressure in the arm 4, with the water passing the sample 5 and exiting through the duct 6. Both regimes can be applied to the inventive device, method, and analysis.

Figure 3:
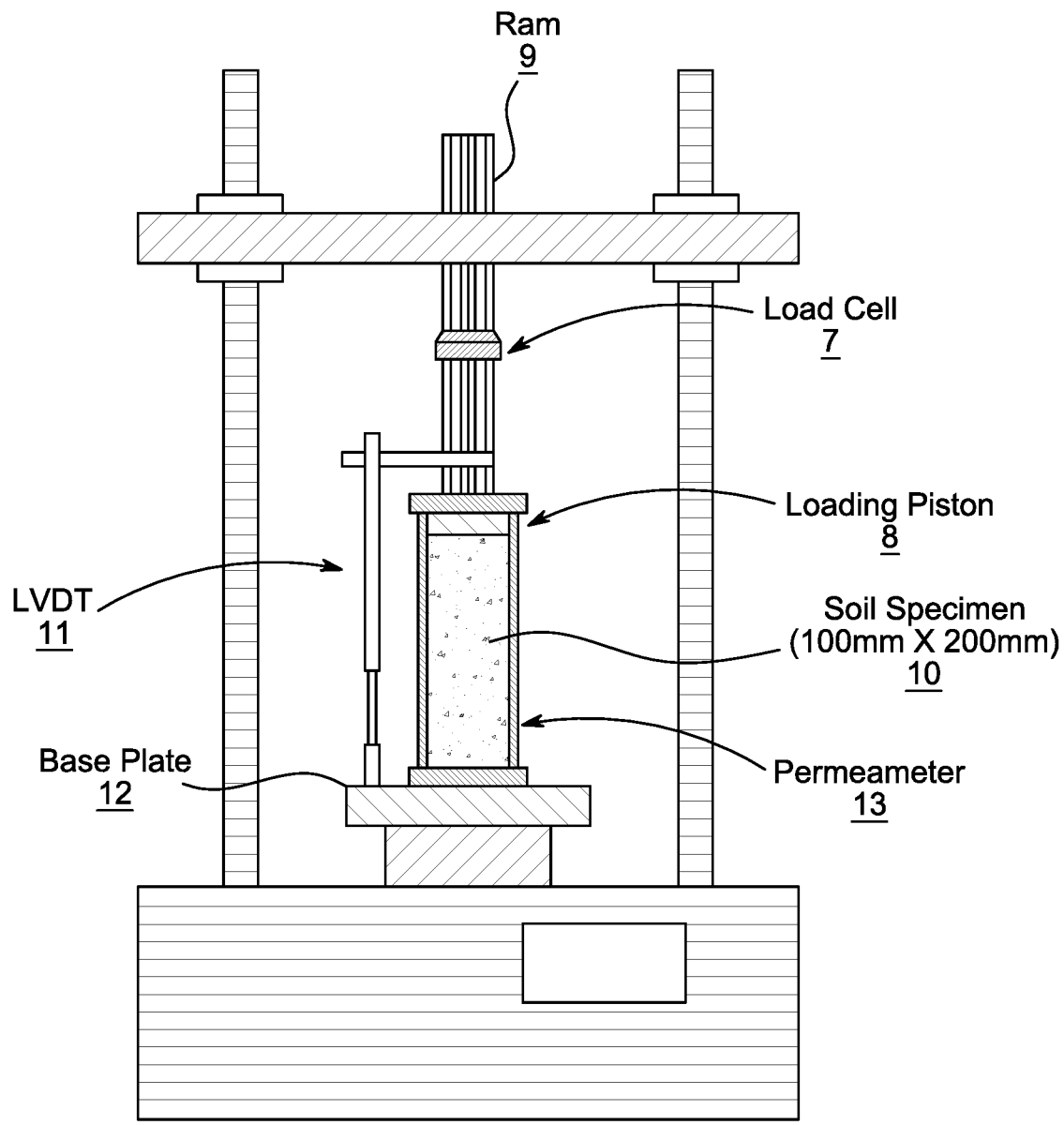
FIG. 3: Lateral cross-section of a hydraulic permeability measurement cell.
Figure 4:
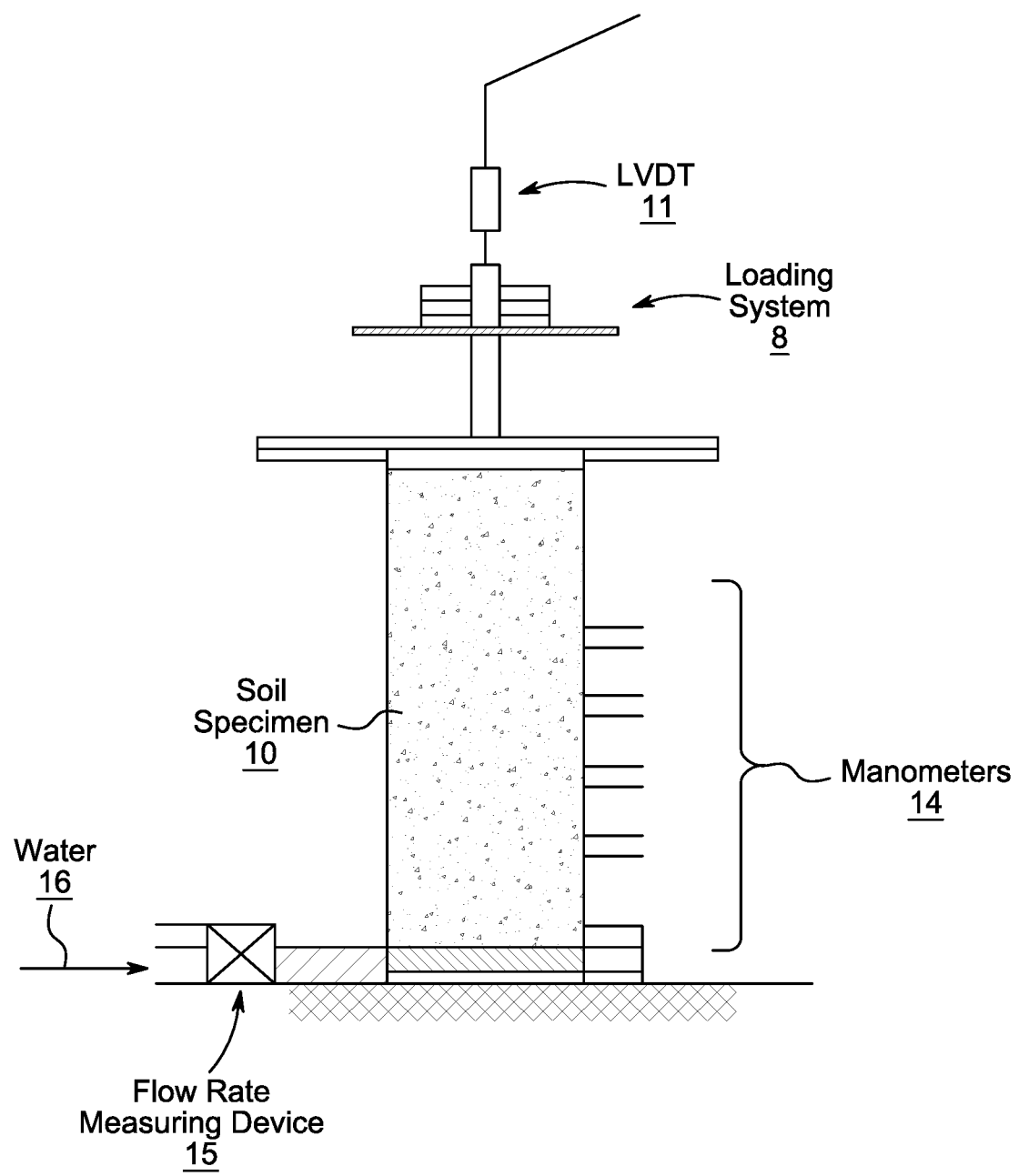
FIG. 4: Attachment scheme for the manometers in the inventive device.
Figure 5:
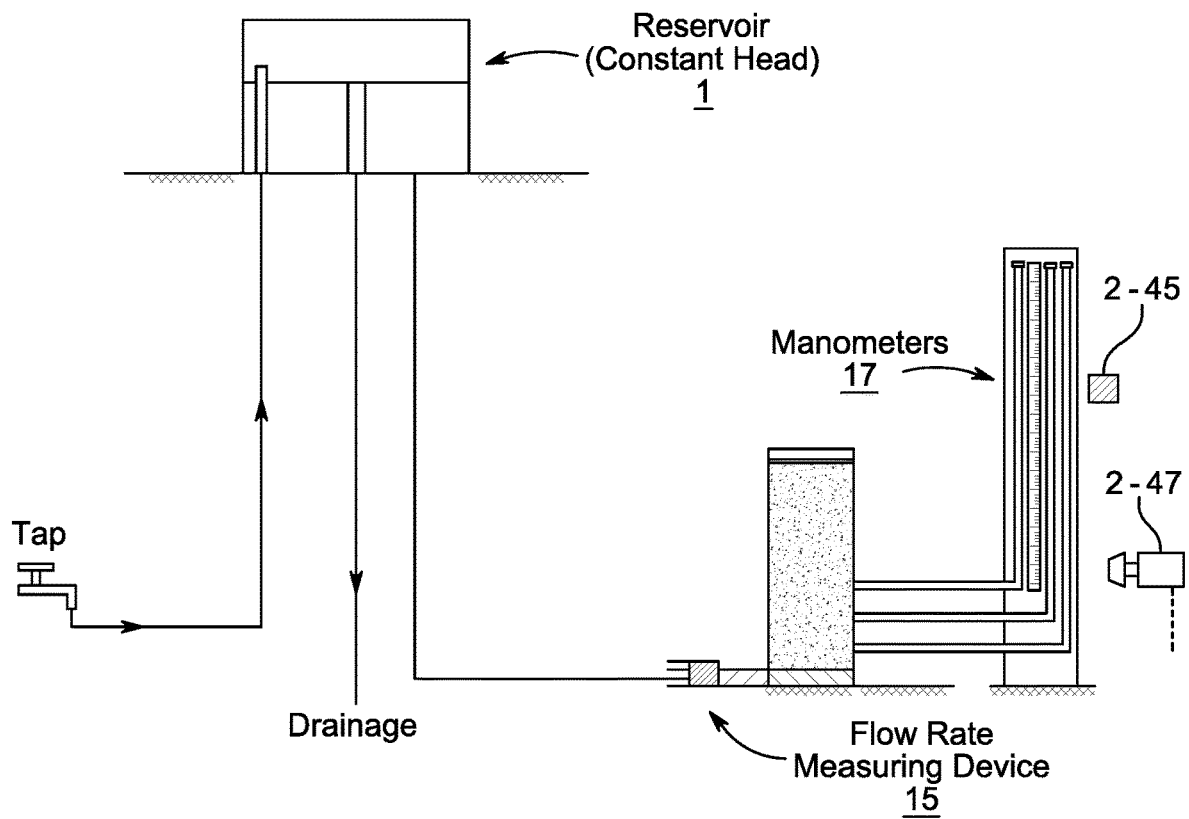
FIG. 5: Assembled experimental scheme.

FIGS. 3-6 present the components of the measuring device. The central element is the enclosure 13 encompassing a sample of soil 10, extracted in-situ or loaded from a storage such as a soil sample collection as a non-limiting example. Loading cell 7 and plate 8 pass the compression stress on the soil sample 10, deforming it and changing its porosity and hydraulic permeability. The relative compression (measured as the ratio of change in the vertical dimension related to the initial sample height) is detected by a linear variable differential transformer (LVDT) sensor. The LVDT converts a position or linear displacement from a mechanical reference (zero or null position) into a proportional electrical signal containing phase (for direction) and amplitude (for distance) information. The LVDT operation does not require an electrical contact between the moving part (probe or core assembly) and the coil assembly, but instead relies on electromagnetic coupling (below). The base plate (porous disk) 12 provides mechanical support to the pressurized permeation cell 13, as well as a conduit for the incoming flow of water 16. The specimen is brought to the intended compression in a permeability cell, and water is passed through it from a constant level tank (FIG. 3-5). As mentioned previously, take-off points located along the sides of the permeability cell are connected to five manometer tubes mounted on a free-standing panel complete with a meter scale. These manometers are manufactured from transparent plastic with the attachment for wall mounting. Water passing through the specimen is collected and measured, either for a specific quantity or over a period of time. The reduction of head at any time is noted from the variation of water level in the manometer tubes (see the analysis below)

Figure 6:
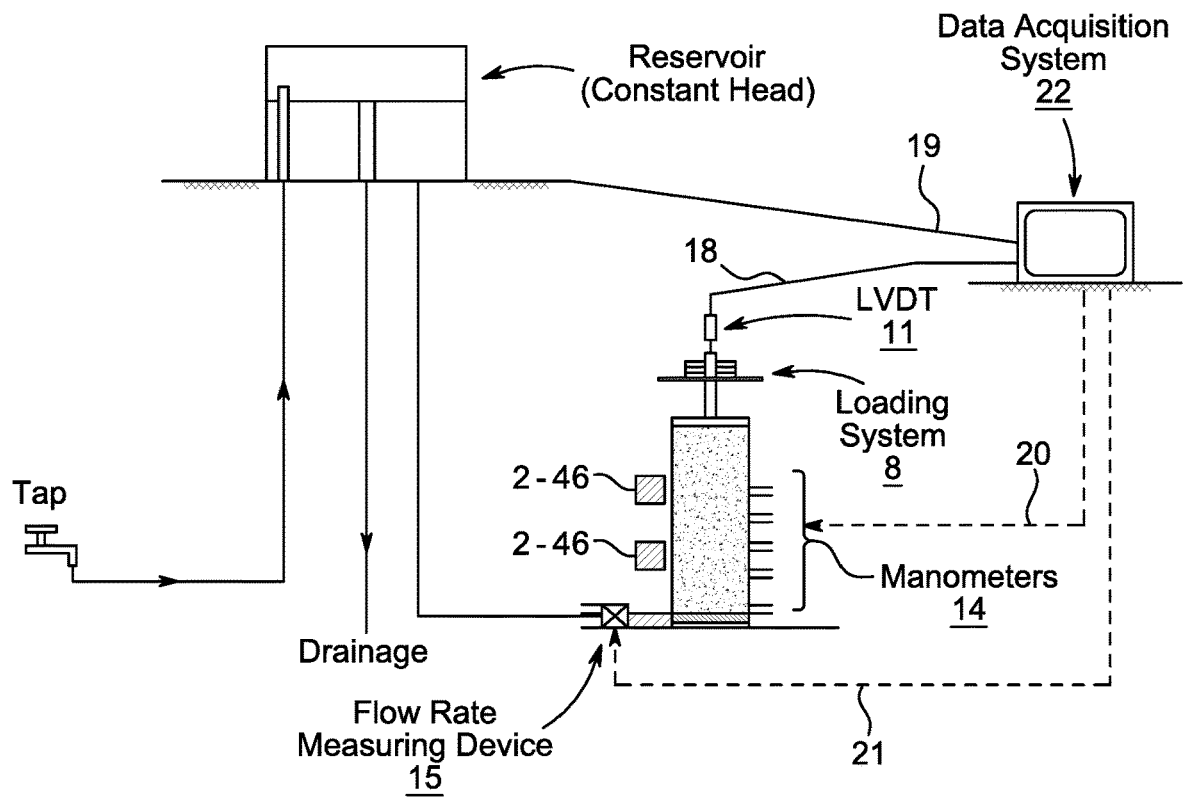
FIG. 6: Synchronized inputs for the data acquisition system.

Aspects of the apparatus for determining hydraulic conductivity of porous formations include a cylindrical pressurized cell shown (2) in FIG. 1 that includes entry (2-1) and exit (2-2) lines for the ingress and egress, respectively, of water flow. After a sample is placed in the pressurized cylindrical cell (2) a lid (2-3) may be used to close the sample cell compartment. A plurality of detectors is utilized to collect useful information for determining properties of the sample. Such detectors may include a detector on the exit line (2-42) and/or entry line (2-41), respectively in FIG. 1. The cylindrical pressurized cell may include one or more detectors for measuring properties such as vertical and/or lateral compression or mechanical deformation of sample (2-43) in the cylindrical pressurized cell (2). As shown in FIG. 5, the manometers (17) may have one or more detectors (2-45) utilized for measuring or identifying the manometer level. A video camera (2-47) can be used to concurrently detect and identify the level of a plurality of manometers (17). FIG. 6 alternately identifies a plurality of detectors (2-46) that may be used to measure properties or conditions such as lateral/vertical compression or mechanical deformation of a soil sample present in the cylindrical pressurized cell.

FIG. 4 shows the water supply duct 16 entering the cell 13 via flow rate measuring device 15. The incoming water percolates porous support disk 12, which is designed with a sufficient hydraulic resistance of at least 0.5 or more taking the soil sample as the reference unit. The hydraulic resistance in 12 ensures even distribution of the incoming flow, entering through the center across the disk volume and simultaneous piston-like motion of every layer up the soil load. The rising ideal displacement (piston) flow through the cell passes the entries of the manometers 14, 17 and, in each of them changes the instant value of water height. These heights would have been equal to the height of the water reservoir 1 (FIG. 1) under static equilibrium conditions when the two vessels equilibrate. Also, the final heights of the menisci in each wall manometer tubes 14, 17 would have been equal under the equilibrium static conditions too.

However, the observed heights in the manometers 17 (FIG. 5) are lower due to pressure losses when water migrates through the pores of the soil experiencing friction.

The normal size of the soil specimen 10 is 200 mm in height (z) by 100 mm in diameter (2R). The sample is subjected to a fixed axial load which emulates geostatic pressure on the soil elements. The application of the load on the top of the cell is provided or guaranteed by means of a ram 7-9, as shown in FIGS. 3 and 4. The sample tested has its ends sealed by top cap and bottom pedestal 13 by rubber O-rings. The axial displacement of the specimen during loading and saturation is measured by means of an LVDT 11 mounted on the side of the cell 13.

Take-off points 14 located along the sides of the permeability cell are connected to five manometer tubes 17. The five plastic flexible tubes are of 3 to 5 mm diameter bore and approximately 1.4 to 1.6 m long. The plastic tubes are fitted to a panel or wooden stand for wall mounting, and they are connected to outlet valves. The inlet, outlet and overflow pipes are fitted to the base of the tank 13 and can be adjusted for height within the tank 13. The observed distances between the theoretically highest point of the menisci in the wall manometers 17 and the positions observed in the dynamic flow-through regimes are proportional to the loss of hydrostatic pressure in the porous media, with the kinetic energy of the flow assumed to be negligible (according to the Bernoulli equation). The pressure balance of each manometer tube is:

$$H = H\text{obs} + \Delta P(z)/dg \quad (11)$$

Where H is the total height of water column available at the bottom of the measurement cell 13 (theoretically equals the level in the tank 1), $H_{obs}$ are the observed meniscus heights in the manometers 17, $\Delta P(z)$ are the pressure losses at the heights z from the bottom of the cell 13, d is the water density, g is the Earth's gravity acceleration. In stationary conditions, when the soil is a granular sand sample with rigid non-swelling particles and unchanged porosity fraction, as well as no clumping, the pressure loss per a unit of distance z is constant along the z-axis of the permeameter 13, G=0, dh/dt=0 (as per stationarity). Equation (10) simplifies as:

$$\frac{d\left(\frac{dh}{dz}\right)}{dz} = 0 \quad (12)$$

$$\frac{dh}{dz} = const \quad (13)$$

Integration of (13) leads to a variation of Darcy's equation (1) for the pressure loss in a porous medium:

$$\Delta H = H(1) - H(z) = nzQ/K\pi R2 \quad (14)$$

Where:
ΔH—is the loss of head measured as the difference between water level H(z) shown by the meniscus in the n-th manometer and 1-st manometer in the series 17;
n—is the number of equidistant intervals between the manometer entries;
z—is the distance between the adjacent manometer entry [m]s;
Q—is the volume flow measured through the device [m³/sec];
K—is the permeability of interest [m³/m² sec];
πR²—is the area of the bottom of the device 13 [m²].

Under the conditions (12)-(14), the sequentially installed manometers (17) would have shown unchanged values of K, measured at variable levels z (5 levels available in this design, with n=4 intervals between). At the lowest level (coinciding with the base plate/disk 12), the friction losses are minimal, and the manometer installed at this level displays the meniscus at the height almost equal to that of the reservoir 1. The manometers installed at progressively increasing heights z register progressively increasing hydraulic pressure losses and therefore the positions of the menisci in the upper manometers are lower in proportion to z. The distance z between the bottom of the measurement cell and the reporting manometer is arbitrary for the case of rigid soil (sand, gravel, limestone). For example, z can be the distance between the first manometer entry at the bottom and #2, 3, 4, 5 or others without limiting. The loss of head H is linearly proportional to z, according to (14). This is a partial non-limiting case, and in general the relations are more complex (below).

The manometer readings, the inflow Q and out-flow Q, as well as timing of each observation, are measured by a controller 22 with the datalinks 18-21. All measurements are synchronized and recorded to address non-stationary regimes. Under the conditions of (14), the inflow equals outflow, and the manometer readings are linearly proportional to the entry distances from the bottom. In non-stationary regimes, this is not the case and each manometer must be tracked individually as a function of time and position. The inflow and outflow volumes are not equal generally, but for longer observations when the passing volume of water significantly exceeds the volume of the measurement device, this imbalance is negligible. The relative displacement (i.e. the strain) of the specimen at time (t) under a given load is deduced from the LVDT measurement and is received by the controller 22 in FIG. 6. The results of the permeability and the associated strain are presented in a graph which gives the variation of the permeability of the soil with strain (or settlement) under a given load during the process of saturation or inundation. This permeability itself can be a constant value, a linearly drifting value, an exponential function or an arbitrary function with or without an asymptotic limit.

Putting G=0 (no imbalance between inflow and outflow), equation (10) can be re-arranged:

$$K = -Ss\left(\frac{dh}{dt}\right)/\left[\frac{\partial 2h}{\partial z2}\right] \quad (15)$$

Where K is the permeability, Ss is the capacity of the testing volume to accumulate water (swelling, porosity, hydration), dh/dt is the rate of hydraulic pressure change, $\partial^2 h/\partial z^2$ is the second derivative of the hydraulic pressure as a function of vertical coordinate. The time and coordinate dependence of the positions for each meniscus in each manometer is carefully recorded by the controller 22 via the sensors and links 18-21. The initial position of each meniscus migrates in time in a non-stationary regime. Assuming that the time-dependent changes in the soil specimen are homogenously distributed through the volume of the apparatus, the time-dependent changes of the levels in each manometer are equal. However, the levels themselves and the spacing between the menisci are not. Yet for the gradual plastic deformations and structural re-arrangements that take place in clay- or humus-rich soils, the $\partial^2 h/\partial z2$ value can also be assumed to remain constant. For example, and without limiting, the meniscus heights in the manometers 1-5 can be: 120, 110, 102, 96, 92 as a function of placement height z in the testing apparatus 13. Each difference is smaller than the previous by the same quantity, enabling a constant second derivative value in (15) and producing a constant value of K in a non-stationary process (changing head pressure is the cause of non-stationarity).

In an alternative embodiment, the permeability constant K is time dependent. This scenario is the most likely for the case when the soil experiences constant compressive load progressively deforming the pores and interstices, or when the temperature of the environment or salinity of the percolating water changes, or when the percolating water has high turbidity producing deposits in the pores of the soil. All these situations conceivably take place under the bottoms of water ponds, storages, waste depositories, aquifers, fracking installations, around artesian wells, riverbeds at different times of a year, under the construction sites or buildings. Time-dependent permeability profile is the most demanded information in such measurements.

In a preferred embodiment, the sensor data collected by the datalinks 18-21 (FIG. 6) are sub-divided in time intervals, each incorporating not less than 1000 data points, preferably 2000, even more preferably 10000 time-dependent measurements. Achieving such measurement density is routine for a conventional processor analyzing only a few readings at once (inflow volume, outflow volume, the positions of the menisci in the manometers, compression, sample deformation, temperature). In a preferred embodiment, the measurements are recorded once per second, preferably twice per second and even more preferably ten times per second within several days of the experiment. The experiment ends when the permeability becomes constant including zero value or when the trend becomes easy to extrapolate to a duration that is beyond the range of the experiment (exponential or polynomial time-course of the permeability value).

In a preferred embodiment the cell 13 is mounted on the electronic scale. weighing the apparatus in a time-dependent fashion to follow the accumulation of water in the chamber (G). Alternatively, the difference flow-meter readings for the incoming and exiting flows may indicate water accumulation, but the second method is less sensitive. The accumulation information is required for the identification of the permeability using the full form of the equation (10), not assuming that G=0.

Not all soils are amenable to the constant head measurements. The preferred soils include granular non-cohesive, silt-free specimens. There is a possibility that under a constant pressure, a highly deformable soil self-seals the pores and stops permeation entirely. Such clay- or silt-rich soils and deposits need to be analyzed by a different approach, wherein the pressure changes over a continuum of values and as the soil compacts under the initial pressure, the said pressure decreases in a predictable fashion delaying this self-sealing deformation. At a certain lower pressure, the soil stops responding with the self-sealing deformation and permeability becomes stable. Alternatively, the pore self-sealing persists through the entire range of pressures and the sample allows passing of a limited volume of water before self-sealing entirely.

FIG. 2 illustrates a Falling Head method, which does not rely on the indefinite preservation of permeability. Instead, the level of water in the tank 1 and line 16 continues to fall in proportion to the volume that passed through the specimen. Under these assumptions, the permeability is found by equation (16) below.

For the falling-head permeameter, the water level in the falling-head tube drops (FIG. 2), and then head measurements are recorded frequently until no flow occurs in the permeameter. In the falling-head method, the soil sample is first saturated under a specific head condition. The water is then allowed to flow through the soil without adding any water, so the pressure head declines as water passes through the specimen. The derivation of working relationship begins with the Darcy's Law:

$$\frac{\Delta V}{\Delta t} = -K h \left(\frac{A}{L}\right) \quad (16)$$

The decrease in volume is related to the falling head by $\Delta V = \Delta h\, A$. Substituting this relationship into the above, and taking the limit dt=0 leads to the differential equation:

$$\frac{dh}{dt} = -(K/L)h \quad (17)$$

Equation (17) has a solution:

$$h(t) = h_i \exp\left(-\frac{K}{L}(t - t_i)\right) \quad (18)$$

where h(t) is the hydrostatic head at the time t, $h_i$ is the initial value, K is the permeability of interest, L is the length of the device (from top to bottom of the cell 13 in the z direction). After elementary transformations, the equation (18) becomes:

$$K = \left(\frac{L}{\Delta t}\right) \mathrm{Ln}\left(\frac{h(t)}{hi}\right) \quad (19)$$

The study of the soil starts with the preliminary assessment of suitability for the constant head method. If the permeability collapses to zero without accepting an asymptotic value, the equation (19) and experimentation revolving around this model is a preferred embodiment.

In a preferred embodiment, the experimentation is standardized and follows a testing method such as those described by ASTMs and that allows interoperability with other methods or standards (ASTM D2434; BS 1377 Part 5; AASHTO T215, titled "Standard Test Method for Permeability of Granular Soils (Constant Head)"). The accompanying standards are D2435 titled "Test Methods for One-Dimensional Consolidation Properties of Soils Using Incremental Loading"; D4767 titled "Test Method for Consolidated Undrained Triaxial Compression Test for Cohesive Soils"; D6169 titled "Guide for Selection of Soil and Rock Sampling Devices Used With Drill Rigs for Environmental Investigations"; E691 titled "Practice for Conducting an Interlaboratory Study to Determine the Precision of a Test Method"; each incorporated herein by reference.

Components of the Measurement System

A main component of the apparatus is the permeameter cell 13. In some embodiments, the cell is made of durable transparent plastic such as acrylic and polycarbonate, allowing dye tracer mapping of the fluid paths and capable of withstanding the overpressure resulting from the load applied on the sediment or soil in the chamber. The typical over-pressure range is 0.2-15 atm, 0.5-10 atm, or 1-5 atm, reflecting the depth of the water-conducting layer and the need to model the geostatic pressure in the laboratory conditions to assess the long-term water-tightness of the soil or rocks at the bottom of water reservoir. The presence of overpressure induced by the load system 7-9 is not sensed by the percolating water since it can escape upstream or downstream of the cell 13, without compression of the adjacent electronic orbitals, which would take place in a closed space. However, the soil or sediment is enclosed, and therefore compressed resulting in smaller pores and generally lower permeability in most of cases.

A percolated soil sample has a fluid-like rheology (for example, rigid sand particles pass pressure to the walls in almost the same manner as true liquid elements). While water flows through the interstices of the compressed sample, the solid elements of the sample exert pressure on the containing walls according to Pascal's Law (in all directions). The walls of the enclosure 13 must be durable enough to withstand the entire range of working conditions (the sum of the hydrostatic pressure of water and the load from the piston directed to the deformable sample). Furthermore, the presence of multiple manometers on the same side may weaken the structure and require greater compensatory thickness.

In some embodiments, the permeameter cell is commercially available and/or customized by drilling additional opening(s) and incorporating the additional manometers. A specialized manufacturer such as Humboldt (see: https://www.humboldtmfg.com/constant-head-permeameter-cells.html) produces a partial set of equipment, including constant head tanks and controllers, that may provide components of the present method and apparatus. However, conventional devices are not provided with the sample compression system 7-9. Customization of a commercially available device may be more difficult than the production of a laboratory version with originally all required features.

In a preferred embodiment, a robust high-pressure device 13 (FIG. 7) allows the analysis of an entire range of experiments—stationary and non-stationary, with saturated and unsaturated soils, with low and high permeabilities that require lower and higher hydraulic pressure as well as multiple levels and directions of sample compression, including triaxial compression. Even more preferably, the permeameter can also serve as a porosimeter, relating the structural data and changes to permeability values. Even more preferably, the permeameter can be used in the analysis of any sediments and not only soils such as filter cakes, shales, geological formations, porous carbonates and sandstones.

Figure 7:
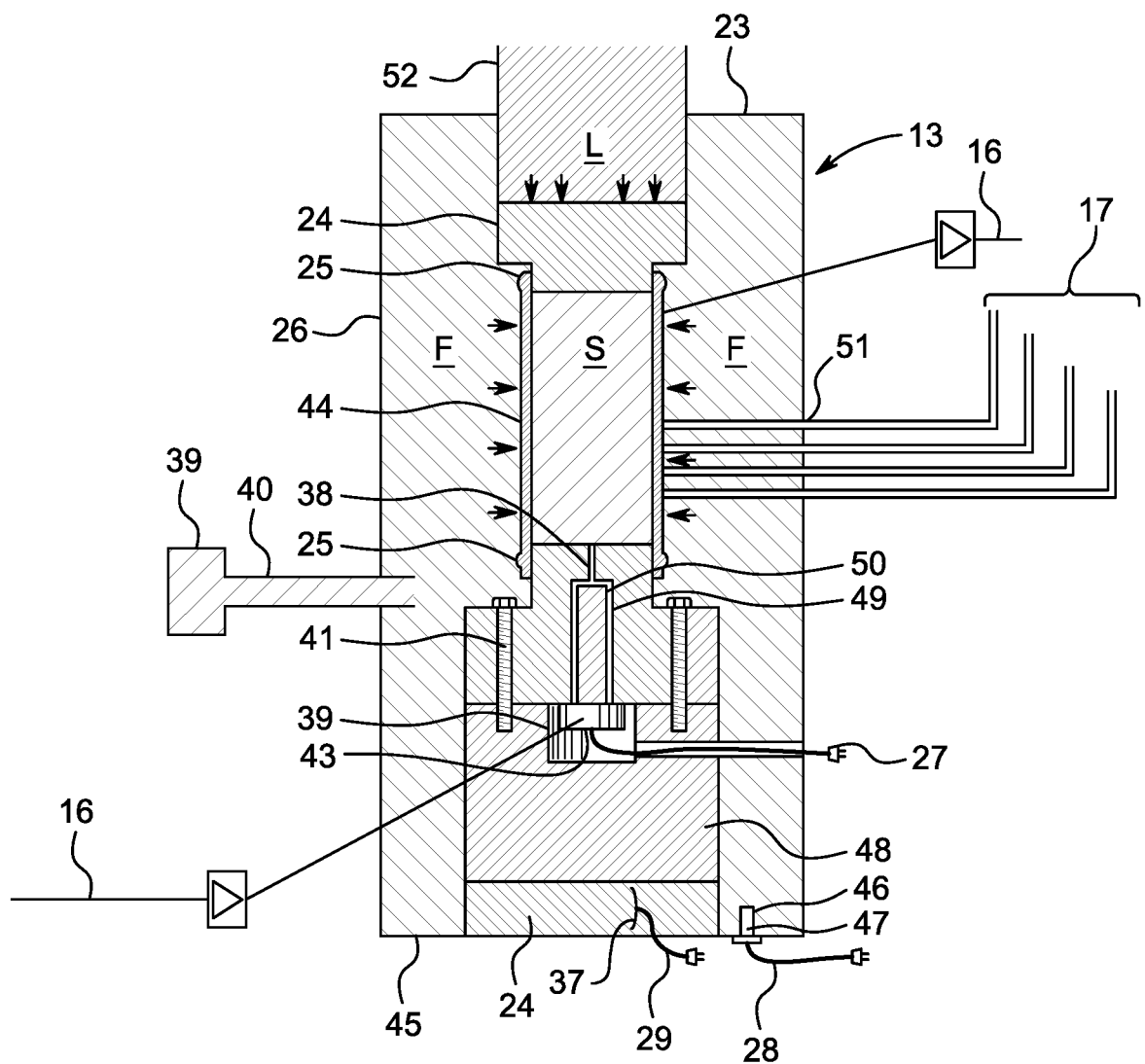
FIG. 7: Detailed side view of a pressurized permeameter adapted for stationary and non-stationary measurement regimes.

As shown schematically in FIG. 7, a triaxial test apparatus 13 according to the present invention has a housing 26 preferably made from titanium or high strength steel with a side wall 51, (preferably generally cylindrical) a bottom plate 45, and a top plate 23. The apparatus 13 has a top-end cap 52, and a bottom cap comprising a top portion 41 and a bottom portion 48 bolted together by bolts 53. The bottom portion 48 rests on a load cell 24 that rests on the bottom plate 45. A sample S, placed between the end caps, is sheathed with an impermeable jacket 44. A load piston 52 contacts the top end cap 24 and a portion of the piston extends (in a sealing manner) through the top plate 23 of the housing 26. The load piston applies a load L to the sample S through the top end cap 24. A confining fluid pumping system 39 pumps hydraulic fluid F into the housing 26 through a fluid line 40. As noted, additional jackets 44 may be used (for example, a flexible plastic jacket passing the confining fluid pressure to the sample without allowing the fluid to penetrate its interstices). The end caps 24, 41 are made from high strength materials (e.g. titanium or hardened steel) and the boundaries between the end caps and the jacketed sample are impermeable. The jacket extends slightly beyond the sample on the end caps and wire ropes 25 secure the ends of the jacket about the end caps.

The end caps have flat, polished smooth surfaces for contacting the sample with diameters closely matched to that of the sample; i.e. it is preferred that they be within 0.005 inches of each other. Also, it is preferred that the flatness of the samples ends be within about 0.001 inch per inch of diameter. This minimizes void space between end cap and sample; provides uniform loading of the sample; and minimizes unwanted end effects.

The device is adapted to assess the dimensions of the soil pores and interstices under different compressive loads and relate the data to permeability. The bottom end cap 41 has a pore pressure channel 38, which communicates with a fluid port or chamber 50. A pore pressure transducer 49 is located in the fluid chamber 50. The bottom portion 48 has a recess 39 therein to provide an area into which a base 43 of the transducer 49 can extend. A non-wetting inert fluid immiscible in water or pore fluid (e.g. mercury) is placed in the pore pressure channel 38 and in the fluid chamber 50. Preferably, the pore pressure channel 38 and the fluid chamber 50 are vacuum evacuated prior to the introduction of mercury so that no air is trapped therein which could adversely affect test results. The pore pressure transducer 50 is an accurate miniature strain-gauge type pressure transducer interfaced via wiring 27 with a digital data acquisition system monitor/control (e.g. computer).

The hydraulic fluid F surrounding the sample S provides an optional confining pressure for the sample S. An embodiment with confining pressure is relevant for porosity measurements, and only vertical axial compression suffices for fluid permeability. However, adding a flexible plastic wrap to the jacket 44 produces an annular space between the sample S and the rigid wall of 44. The confining fluid in this annulus laterally compresses the soil sample. A confining pressure transducer 25 mounted in a hole 46 in the plate 45 has wiring 28 leading to a computer/processor. The load cell 24 has wiring 29 extending therefrom for interfacing with the computer. The load cell 24 has a strain gauge (or gauges) 37 thereon that indicates the amount of axial load applied through the top end cap and to the sample by the piston 52.

The axial pressure system is more relevant to the permeability measurements, and the metal walls of the test cell, as described above are compatible with most regimes. The lines 16 with the valves displays the flow of clean, filtered water entering and exiting the sample chamber. The serial manometers 17 are shown to extend out of the right sidewall of the cell in FIG. 7.

The piston 24 is provided with a servo-control 18 (FIG. 6) and is actuated hydraulically. The servo-control is synchronized with the flow meters and manometer reading, with the values of the pressure on the sample accompanying other indicators collected by the controller 22. Once the pressure of interest is achieved, the position of the piston 24 is fixed, and the system reaches a true or pseudo-stationary state according to the specimen permeability response.

The cell 13 is provided with multiple sensors such as flow meters (line 16), level detectors installed on the manometers, LVDT displacement sensors, compression sensors, thermometers, weighing scales. Operation of these sensors is not trivial, for example, the inductive principle of flow detection depends on electric conductivity of the water flow passing a magnetic contour. After contacting soil samples, the conductivity values increase and are likely to produce an artifact by this method. Weighing on a sensitive scale implies that all parts are motionless.

Regarding flow-meters, Venturi type, Orifice plate, Dall tube, and Pilot tube are preferred embodiments without limiting, due to the principle of functions. These meters function by producing an obstacle in a flow, constraining the flow, and increasing its velocity according to the Bernoulli equation. On the other side of the meter, the flow expands and decelerates. The pressure difference between the accelerated and decelerated regions forms the signal, which is not perturbed by variation in conductance after extraction of electrolytes from the soil sample (See Liptak B G. Flow measurement. CRC Press; 1993 Sep. 15; Prabu S V, Mascomani R, Balakrishnan K, Konnur M S. Effects of upstream pipe fittings on the performance of orifice and conical flowmeters. Flow Measurement and Instrumentation. 1996

Mar. 1; 7(1):49-54; Xu Y, Wu J W, Zhang Q, Li G, Li Q Z. Numerical simulation for cone style differential pressure flow sensor. Chinese Journal of Sensors and Actuators. 2007 October (10):45; Reader-Harris M. Differential Pressure (DP) Flowmeters. Handbook of Measuring System Design. 2005 Jul. 15; each incorporated herein by reference in entirety).

The type of sensors suitable for detection of the levels in the manometers include "level sensors". Level sensors detect the level of liquids and other fluids and fluidized solids, including slurries, granular materials, and powders. Substances that flow become essentially horizontal in their containers (or other physical boundaries) because of gravity whereas most bulk solids pile at an angle of repose to a peak. The substance to be measured can be inside a container or can be in its natural form (e.g., a river or a lake). The level measurement can be either continuous or point values. Continuous level sensors measure level within a specified range and determine the exact amount of substance in a certain place, while point-level sensors only indicate whether the substance is above or below the sensing point. Generally, the latter detect levels that are excessively high or low (see Henry Hopper, "A Dozen Ways to Measure Fluid Level and How They Work," Dec. 1, 2018, Sensors Magazine, retrieved May 19, 2020, incorporated herein by reference in its entirety).

Typical systems for point level detection in liquids include magnetic and mechanical floats, pressure sensors, electroconductive sensing or electrostatic (capacitance or inductance) detectors—and by measurement of a signal's time-of-flight to the fluid surface, through electromagnetic (such as magnetostrictive), ultrasonic, radar or optical sensors. Continuous level sensors relay the exact level of a tank or vessel at any point, over a full span of measurement. This is most often used for process control or any application when absolute precision and accuracy are of crucial importance, and such precision is preferred for the inventive method. Manufacturers such as Drexelbrook provide a broad range of continuous level sensors. The company produces level sensing devices based on the principles of RF admittance, ultrasonic, open-air radar, guided wave radar, magnetostriction.

In a preferred embodiment, a video-camera with high resolution/pixilation characteristics (5000×5000 per cm$^2$) can be installed in a defined position, and the differences between the manometers can be measured optically (U.S. Pat. Nos. 5,747,824, 7,956,341, Petrov I. Raspberry Pi based System for Visual Detection of Fluid Level. Capstone thesis project, Tallinn University of Technology. 2014; Chakravarthy S, Sharma R, Kasturi R. Noncontact level sensing technique using computer vision. IEEE transactions on Instrumentation and measurement. 2002 Aug. 7; 51(2):353-61; Chandani S M, Jaeger N A. Optical fiber-based liquid level sensor. Optical Engineering. 2007 November; 46(11): 114401; Singh H K, Chakroborty S K, Talukdar H, Singh N M, Bezboruah T. A new non-intrusive optical technique to measure transparent liquid level and volume. IEEE Sensors Journal. 2010 Sep. 23; 11(2):391-8; Ritterbusch K, Junginger S, Thurow K. Camera grids for laboratory automation. In 2012 IEEE International Instrumentation and Measurement Technology Conference Proceedings 2012 May 13 (pp. 1352-1357). IEEE; each incorporated herein by reference in entirety).

In some embodiments, the measurements are taken manually by the experimenters. These measurements are precise if the manometer tubes are thin and the time-dependent processes are relatively slow. The experimenter can either photograph or record the position of each meniscus at certain time intervals and import this information for computational analysis.

The type of sensors adapted to measure the compression strain in the z, x and y dimensions include LVDT (Linear Variable Differential Transformer) meters. The linear variable differential transformer (FIG. 8) has three solenoidal coils 54 and 56 placed end-to-end around a tube 55. The center coil 54 is the primary, and the two outer coils 56 are the top and bottom secondaries. A cylindrical ferromagnetic core 57, attached to the object whose position is to be measured, slides along the axis of the tube. An alternating current drives the primary and causes a voltage to be induced in each secondary proportional to the length of the core linking to the secondary. The frequency is usually in the range 1 to 10 kHz.

As the core 57 moves, the primary's linkage to the two secondary coils changes and causes the induced voltages to change. The coils are connected so that the output voltage is the difference (hence "differential") between the top secondary voltage and the bottom secondary voltage. When the core is in its central position, equidistant between the two secondaries, equal voltages are induced in the two secondary coils, but the two signals cancel, so the output voltage is theoretically zero. In practice, minor variations in the way in which the primary is coupled to each secondary mean that a small voltage is still non-zero when the core is central.

This small residual voltage is due to phase shift and is often called quadrature error. It is a consequence of using synchronous demodulation, with direct subtraction of the secondary voltages at AC. Modern systems, particularly those involving safety, require fault detection of the LVDT, and the normal method is to demodulate each secondary separately, using precision half wave or full-wave rectifiers, based on op-amps, and compute the difference by subtracting the DC signals. Because, for constant excitation voltage, the sum of the two secondary voltages is almost constant throughout the operating stroke of the LVDT, its value remains within a small window and can be monitored such that any internal failures of the LVDT causes the sum voltage to deviate from its limits and be rapidly detected, causing a fault to be indicated. There is no quadrature error with this scheme, and the position-dependent difference voltage passes smoothly through zero at the null point.

When the core 57 is displaced toward the top, the voltage in top secondary coil increases as the voltage in the bottom decreases. The resulting output voltage increases from zero. This voltage is in phase with the primary voltage. When the core moves in the other direction, the output voltage also increases from zero, but its phase is opposite to that of the primary. The phase of the output voltage determines the direction of the displacement (up or down) and amplitude indicates the amount of displacement. A synchronous detector can determine a signed output voltage that relates to the displacement.

The LVDT is designed with long slender coils to make the output voltage essentially linear over displacement up to several inches (several hundred millimeters) long. The LVDT can be used as an absolute position sensor. Even if the power is switched off, on restarting it, the LVDT shows the same measurement, and no positional information is lost. Its biggest advantages are repeatability and reproducibility once it is properly configured. Also, apart from the uniaxial linear motion of the core, any other movements such as the rotation of the core around the axis will not affect its measurements. Because the sliding core does not touch the inside of the tube, it can move without friction, making the LVDT a highly reliable device. The absence of any sliding or rotating contacts allows the LVDT to be completely sealed against the environment. LVDTs are commonly used for position feedback in servomechanisms; thus it is suitable for the present invention to regulate the degree of compression and relative deformation of the soil sample. (see Hearn N, Mills R H. A simple permeameter for water or gas flow. Cement and Concrete Research. 1991 Mar. 1; 21(2-3):257-61; Bauer S J, Lee M Y, Gardner W P. Helium-Mass-Spectrometry-Permeameter for the measurement of permeability of low permeability rock with application to triaxial deformation conditions. Sandia National Lab. (SNL-NM), Albuquerque, N. Mex. (United States); 2015 Feb. 1; Cuss R J, Harrington J F. Effect of stress field and mechanical deformation on permeability and fracture self-sealing. Progress report on the Stress Path Permeameter experiment conducted on Callovo-Oxfordian Claystone; each incorporated herein by reference in entirety).

Temperature influences dynamic viscosity and a temperature gradient within the apparatus may distort the value of hydraulic permeability. Temperature is maintained constant, preferably at 25° C. throughout the building or room where the permeameter is installed. The changes of temperature are recorded to ensure that corrections are possible in the initial permeability values and day-by-day values are comparable. The water column 16 is preferably supplied from an upper floor or a separate building through a pipe (or a flexible tube). Due to extensive surface-to-volume ratio of the conduit the temperature of the incoming water may deviate from the equilibrium value for the rest of the apparatus and a heat exchanger as well as a filtering modules are required upstream of the entry in the cell 13.

Another source of undesired temperature effect is deformation and conversion of mechanical energy into thermal. Larger testing cells with high soil sample volume/hourly water flux ratios may warm up during application of the compressive strain in the inventive apparatus. A slow rate of compression is preferred for generating objective values (See ZHENG Y H, TAO X J. Temperature Monitoring System of Geotextile Permeameter. Journal of Luoyang Institute of Science and Technology (Natural Science Edition). 2014(3):15; Smith J E, Robin M J, Elrick D E. Improved Transient-Flow Air Permeameter Design: Dampening the Temperature Effects. Soil Science Society of America Journal. 1998 September; 62(5):1220-7; each incorporated herein by reference in its entirety).

Filtration is also a preferred element of pre-treatment. Solids from suspensions in the testing water may be trapped and accumulate in the pores of the soil sample, distorting the time-course of the permeability measurement and eventually rendering it unusable. The same possibility exists for off-gassing microbubbles if the water column 16 is high and the water is pumped in the feeding tank, providing the constant hydraulic head to the system (FIG. 1, pos. 1). According to Henry's law, air solubility in water is proportional to pressure, and if there is a water/air contact in the initial pump, the water is saturated at higher pressure. The work of the pump is consumed by elevating each element to the level of the feeding tank 1. At this point, the ambient air pressure should be atmospheric, and the gas exchange surface vs. the volume of the fluid in the feeding tank must be extensive enough to ensure that the excess of dissolved air is vented. In this case, when the pressure of the fluid increases again (water falls down the feeding line 16 to the level of the permeameter, and the entire column produces hydrostatic pressure), the water is undersaturated and is unlikely to off-gas in the pores of the sample.

The datalinks from the servomechanisms (the extent of compression), LVDT (the extent of deformation), thermometers, manometers (the profile of pressure loss), flow meters (the flow value and balance between the incoming and outgoing volume) and the electronic scale (accumulated water mass in the cell) lead to the controller. The controller 22 comprises a digital or an analog computer, chronometer, memory unit, I/O device or recorder, and a cloud communication link with similar apparatuses.

In a preferred embodiment, and without limiting, the controller is customized and assembled on an Arduino template (see Selker A, Drake S A, Selker J S. A Portable Streambed Permeameter Built With 3-D Printed and Arduino Controller/Data-Logger. InAGU Fall Meeting Abstracts 2014 December; Rodriguez-Juárez P, Júnez-Ferreira H E, Gonzalez Trinidad J, Zavala M, Burnes-Rudecino S, Bautista-Capetillo C. Automated Laboratory Infiltrometer to Estimate Saturated Hydraulic Conductivity Using an Arduino Microcontroller Board. Water. 2018 December; 10(12): 1867; Spinelli G M, Gottesman Z L, Deenik J. A low-cost Arduino-based datalogger with cellular modem and FTP communication for irrigation water use monitoring to enable access to CropManage. HardwareX. 2019 Oct. 1; 6:e00066; each incorporated by reference in its entirety). The Arduino-compatible processors are Arduino UNO R3 and the Arduino Mega 2560 processors, without limiting and mentioned solely as illustrating examples. In another embodiment, the controller is analogous to the controller of U.S. Pat. No. 6,212,941 or customized by PMI (see The PMI Automated Liquid Permeability System by PMI Porous Materials Inc., specially designed for testing core samples and its controlling unit is incorporated herein by reference in its entirety).

A water tank serves as a water column reservoir, maintaining a constant hydraulic head in the inventive method. Deviations of the water levels in the tank may lead to inconsistencies in the permeability measurements. The tank is provided with a point level meter of the designs considered above (also see U.S. Pat. No. 4,470,299, ultrasonic level meter; U.S. Pat. No. 6,938,478, impedance level meter for liquids in tanks; Hidayat M R, Sambasri S, Fitriansyah F, Charisma A, Iskandar H R. Soft Water Tank Level Monitoring System Using Ultrasonic HC-SR04 Sensor Based On ATMega 328 Microcontroller. In 2019 IEEE 5th International Conference on Wireless and Telematics (ICWT) 2019 Jul. 25 (pp. 1-4). IEEE; Premi M G, Malakar J. Automatic Water Tank Level and Pump Control System. In 2019 International Conference on Intelligent Computing and Control Systems (ICCS) 2019 May 15 (pp. 401-405). IEEE; each incorporated herein by reference in entirety). While the level is generally stable, the final value can be variable to ensure that there is a sufficient gas-exchange surface at the top of the tank to off-gas quickly.

A feeding pump lifting the water in the tank can be a tap water source, a peristaltic pump, piston pump, turbo pump or a compressed air pump. In a preferred embodiment the water source filling the tank 1 is the conventional water supply tap, provided with a downstream ultrafilter that eliminates the entire range of dispersions and contaminants (see: Lowe J, Hossain M M. Application of ultrafiltration membranes for removal of humic acid from drinking water. Desalination. 2008 Jan. 5; 218(1-3):343-54; Winona L J, Ommani A W, Olszewski J, Nuzzo J B, Oshima K H. Efficient and predictable recovery of viruses from water by small scale ultrafiltration systems. Canadian journal of microbiology. 2001 November 1; 47(11):1033-41; each incorporated herein by reference in entirety).

In another non-limiting exemplary embodiment, the filters are commercially available tap faucet mounts such as Brita® Faucet Mounts; Yescom 5-Stage Hollow Fiber Ultrafiltration Water Filter System; Tap Master Ultra Filter Change Set ISet-TMUL-MY12; Undersink Triple Ultrafiltration Water Filter by FilterWater.com. Ultrafiltration can be supplemented by ion-exchange and activated carbon treatments to eliminate the excess of tap water hardness carbonates, fluoride or organic that may alter the soil properties under long exposure. Alternatively, saline can be added to the tank 1 to maintain the ionic strength at a certain constant level in the range of 0.001-1% for the clay-rich soils that would change the permeability properties due to excessive swelling in a desalinated percolating water.

In case of unavailable tap water—for example in the field conditions—the tank can be installed on a pole, a tree, a hill slope, a bridge. In this case, the artesian, pond or river water is the working fluid and needs to be pretreated accordingly. Also, the pretreated water needs to be pumped in the tank with minimal interference with the experimental results. Use of a piston pump is, for example, problematic due to potential water contamination by pump servicing oils and vibration that would have been passed to the cell 13 via the descending water line 16. Similar complications are expected for a turbo pump, leaving peristaltic pumps as a preferred non-limiting embodiment.

The connecting tubing in the system, especially the tubing providing a hydrostatic head in the line 16 is preferably made of transparent plastic, such as durable polyethylene or polypropylene, including the composites, grafts, and copolymers. The requirement for the tubing is long-term dimensional stability under the conditions of constant pressure load. For example, a line 65 m high would provide 5 atm of excess hydrostatic pressure at the floor level, and the walls of the tubing must endure this pressure for days and weeks of repeated experimentation. Non-limiting examples comprise: Clear-Guard™ High Pressure Clear PVC Pipe by Ipex; Tygon by Greiger Industrial Supply; Apache Reinforced Clear Vinyl Tubing by Northern Tool; Nylon High-Pressure Flexible tubing; MasterFlex tubing etc.

Sample Preparation

The permeability measurements apply to soils, sediments, filter cakes, shales, and porous rocks. Depending on the rigidity of the formation, coring may or may not be conducted. For example, for soft silts or dispersible soils coring is unsuitable and the material is simply scooped and loaded in the testing volume with minimal compaction. For more rigid and ordered formations, coring is a preferred sampling method embodiment since it preserves the natural order of deposition and layering, which can deeply impact the result.

In a preferred embodiment, a well or a ditch is drilled to the depth of interest (can be shallow) and the formation is collected by a core sampler. Soil core sampling equipment is used to collect virtually undisturbed soil core samples for profiling and environmental investigations.

In a preferred embodiment, AMS Inc. (https://www.ams-samplers.com/) offers soil core samplers, split soil core samplers, and multi-stage soil core samplers. All of these quality sampling tools allow the user to collect core samples into removable liners. The split core soil core sampler also allows the user to open the soil core sampler body to view the soil specimen after sampling. Soil core samples may be collected at the surface or from a pre-augered borehole. To collect small diameter, soil cores at or near the subsurface, AMS also offers a variety of soil probes that may be used with or without liners.

Figure 9:
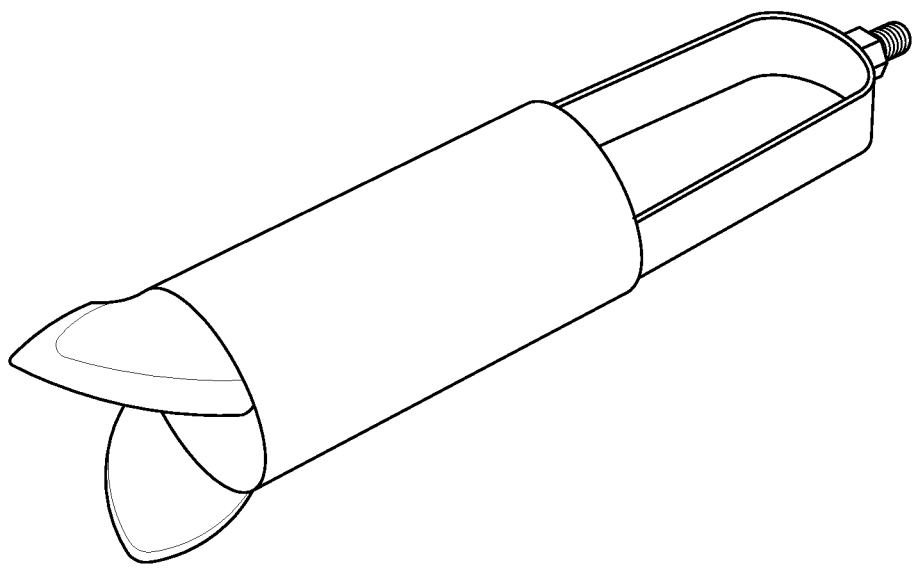
FIG. 9: Regular auger tip tool.
Figure 10:
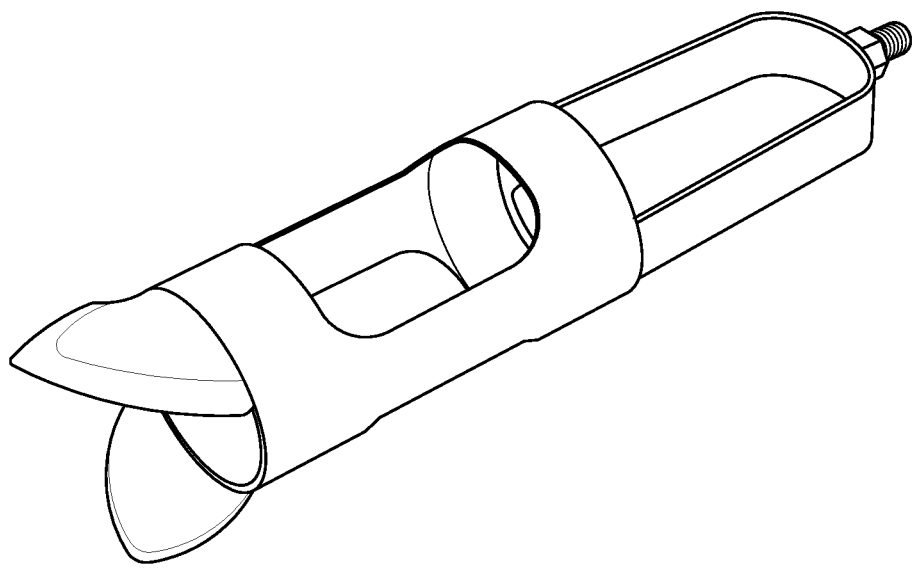
FIG. 10: Mud auger tip tool.
Figure 11:
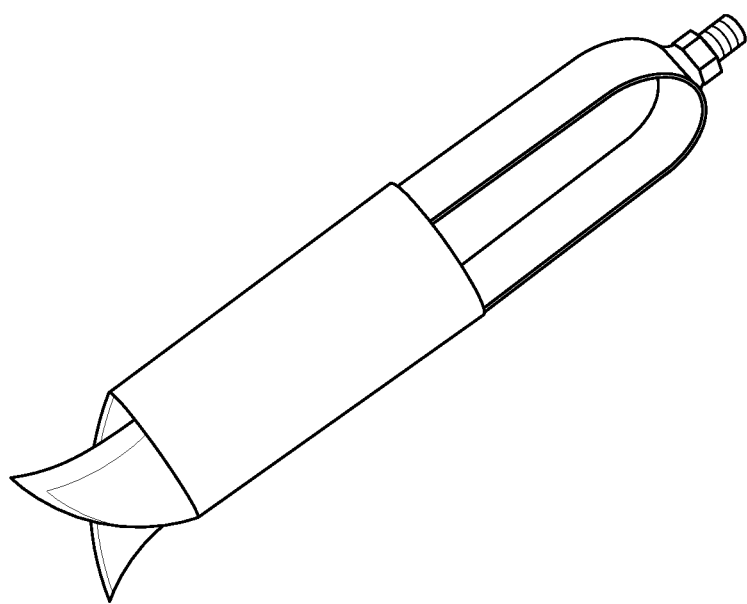
FIG. 11: Sand auger tip tool.
Figure 12:
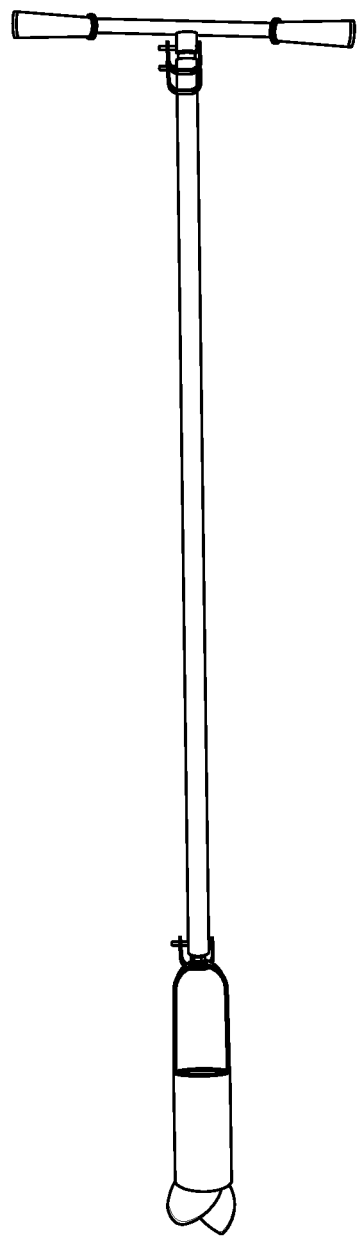
FIG. 12: Assembled sand auger tip with the matching handle for manual soil core extraction.

FIG. 9 presents the AMS regular soil auger commonly used for obtaining disturbed soil samples at or near the surface and for boring to depths where soil samples may be obtained with a separate soil sampler or soil core sampler. The bits of the regular soil auger are open to allow entry of small soil clumps and relatively small rocks and particles. FIG. 10 presents the AMS mud auger that features two openings in the cylinder wall to facilitate emptying as well as wider spaced bits than the AMS regular soil auger to ease entry of sticky soils. FIG. 11 presents the AMS sand auger that use a closed bit design with a restricted opening to prevent the loss of sampled material during retrieval. The sand auger has a cylinder similar to the regular soil auger, but the inner edges of the sand auger bits touch at their mid-point to make the sand auger a much more reliable auger in loose, unconsolidated soil conditions. Many more specialized augers exist for different soil classes, without limiting. In operation, the augers are assembled with a handle termed "connector" allowing rotational movement of the auger tip from the standing position of the operator holding the tool at the belt level (FIG. 12). In another embodiment, the manual augers are produced by SOILMOISTURE Inc, and range in the inner diameter 2.5-10 centimeters, allowing to extract the intact soil slabs comparable in diameter with the cell 13. Once the core with the diameter matching the cell 13 is extracted, it is inserted in the working chamber and the top side is evened by a knife or a roller to distribute the compression by the piston more proportionally. The final step is closing, with the O-rings preventing water exit.

Figure 13:
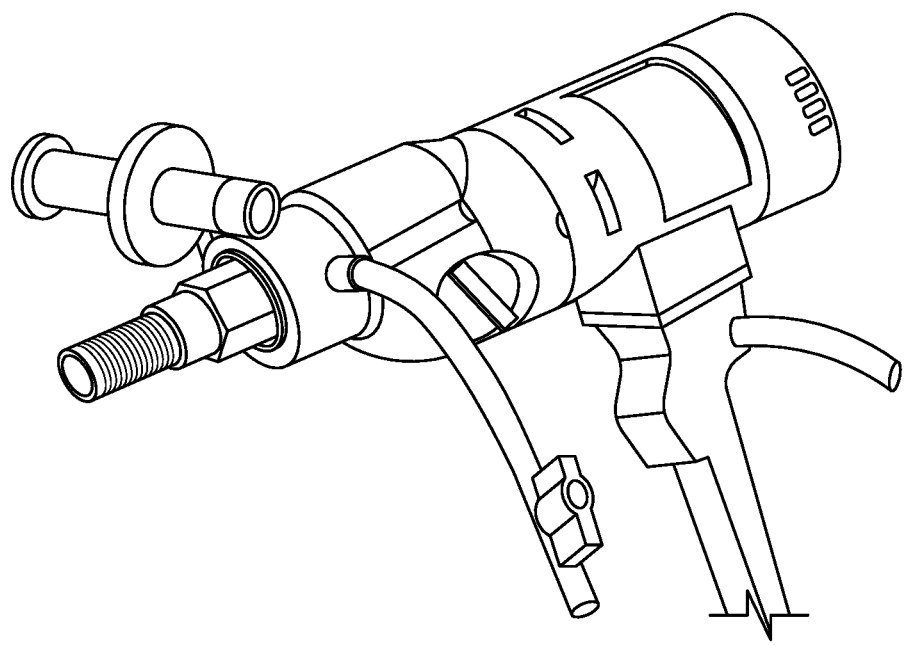
FIG. 13: Outline of a typical powered core drill.
Figure 14:
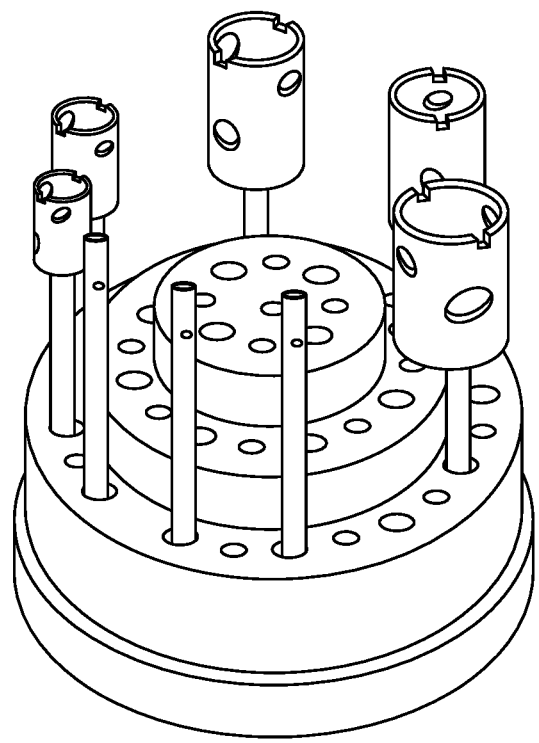
FIG. 14: Drill bits for a powered core drill.

For more intense procuring effort or for harder formations such as shale rocks or porous carbonate/sandstone rocks core drills are used instead of manually operated kits presented above. A core drill is a drill specifically designed to remove a cylinder of material, much like a hole saw (FIG. 13, 14). The material left inside the drill bit is referred to as the core. In operation, the diamond or cermet edge of the cup-like drilling bit (FIG. 14) rotates with speed 500-5000 rpm and penetrates in the substrate, ejecting the pulverized material. The cylindrical core is encompassed by the drill bit and can be isolated by breaking off after the rotating edge enters deep enough.

In another embodiment, professionally extracted cores are collected and can be sold to the research laboratories. Most often, commercial providers manufacture and sell the cylindrical rock cores representing hydrocarbon reservoirs: Kocurek Industries INC., Vinci Technologies, Rockman, Bureau Veritas Commodities Canada Ltd. without limiting. Water permeability of these cores is within the scope of the inventive method since contamination of aquifers by the well-processing fluids is a re-current complain. Ideally, the formation surrounding the oil well subjected to forced extraction should be frackable by water-based working fluids but should not leak the fluids in the absence of fracturing pressure, just under the hydrostatic conditions.

The additional sources of professionally extracted cores are available with the Core Research Center system. Core Research Center was established to coordinate these efforts and preserves valuable rock cores for scientists and educators from government, industry, and academia. Other core depositories include Alabama Geological Survey State Oil and Gas Board Core Warehouse, Alabama Geological Survey State Oil and Gas Board Core Warehouse, Alaska Geologic Materials Center, Alaska Geologic Materials Center Online Inventory, Arizona Geological Survey (AZGS) 1993 Core Repository Report, Arkansas Geological Survey Norman F. Williams Well Sample Library, California Well Sample Repository, Connecticut Geological Survey Bedrock Core Repository, Delaware Geological Survey Outer Continental Shelf Core and Sample Repository, Florida Geological Survey Core and Cuttings Repository, Illinois State Geological Survey Geological Samples Library, Search Illinois Geological Samples Library, Iowa Geological Survey Oakdale Rock Library and Research Facility, Kansas Geological Survey Kansas Core Library, Kansas Geological Survey Kansas Rotary-cutting samples, Kentucky Geological Survey Well Sample and Core Library, Well Sample and Core Library Database Search, LACCORE National Lacustrine Core Repository, Louisiana Geological Survey Resource Center Core Repository, Maine Geological Survey Core Repository and Exploration Records, Michigan Geological Repository for Research and Education, Minnesota Department of Natural Resources Division of Lands and Minerals Drill Core Library, Mississippi Department of Environmental Quality, Environmental Geology Division, Office of Geology, Core and Sample Library Missouri Department of Natural Resources McCracken Core Library and Research Center Nebraska Conservation and Survey Division Geological Sample Repository, Nevada Bureau of Mines and Geology Great Basin Science Sample and Records Library, New Mexico Subsurface Data and Core Libraries, North Carolina Geological Survey Coastal Plain Office Core Repository, North Dakota Geological Survey Wilson M. Laird Core and Sample Library, Ohio Department of Natural Resources Geological Survey Core and Sample Repository, Oklahoma Geological Survey Core and Well Cutting Research Facility, Pennsylvania Department of Conservation and Natural Resources (DCNR), South Carolina Geological Survey Core Repository, South Dakota Geological Survey Core and Cuttings Repository, Core and Cuttings Repository Database, Texas Bureau of Economic Geology Core Research Facilities, Integrated Core and Log Database, Utah Geological Survey Core Research Center, Wisconsin Geological & Natural History Survey Research Collections and Education Center (Core Repository). The USGS maintains the most diverse public-access core collections in the USA. A variety of core sub-collections are available in the repository, including those from oil shale development; Eniwetok Atoll; Cajon Pass, California; Yellowstone Park; and off-shore wells. In addition, CRC curates collections of cuttings (rock chips) brought to the surface during drilling operations. The core and cuttings collection is also accompanied by a large collection of thin sections, which are used to examine microscopic details of the rocks. Images of the thin sections and photographs of some cores are available for viewing and download. Files containing chemical and physical analyses, core descriptions, stratigraphic charts, and various other analyses performed by previous users of the collection can also be downloaded. The CRC houses about 2 million feet of core in the general collection of petroleum exploration and development holes as well as in specialized collections.

In another preferred embodiment, relatively deep wells are drilled in the vertical and slanted directions (see Examples), reaching the aquifer. The depth of drilling is from 1 to 1000 m depending on the aquifer location. The wellbore is stepwise deepened, the conventional drilling assembly withdraws, and the core-barrel/core-catcher assembly is inserted extracting a cylindrical sample of formation at certain levels. A core bit is used to accomplish this goal, in conjunction with a core barrel and core catcher. The bit is usually a drag bit fitted with either metal, PDC or natural diamond cutting structures, but the core bit is unusual in that it has a hole in its center. This allows the bit to drill around a central cylinder of formation, which is taken in through the bit and into the core barrel. The core barrel itself may be thought of as a special storage chamber for holding the formation core. The core catcher serves to grip the bottom of the core and, as tension is applied to the drill string, the formation under the core breaks away from the undrilled formation below it. The core catcher also retains the core so that it does not fall out the bottom of the drillstring, which is open in the middle at that point.

The approach is suitable for accessing the formations of various hardness, with the diamond bit more suitable for rock formations and metal or cermet bits sufficient to collect the soil cores.

Figure 15A:
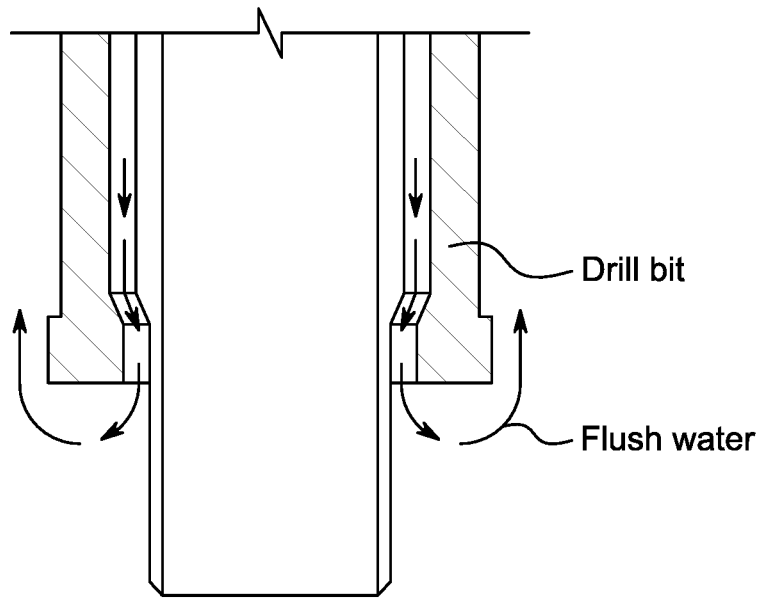
FIG. 15A: Arrangement for core capturing in a softer material.
Figure 15B:
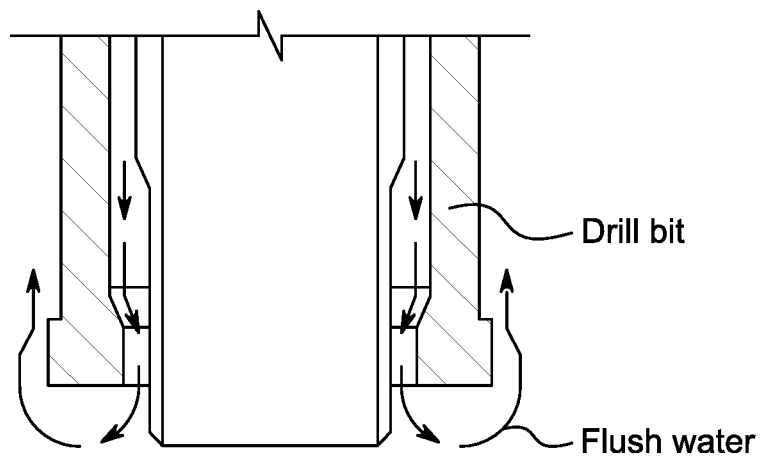
FIG. 15B: Arrangement for core capturing in a harder material.

The embodiment of FIGS. 15A and 15B shows the core capture system for soft materials with high strength and cohesion. After drilling to a position of interest, a hollow and sharpened cylindrical element is extended out of the drill to encompass the core material which adheres to the inner surface of the catcher enough to be broken off.

Figure 16A:
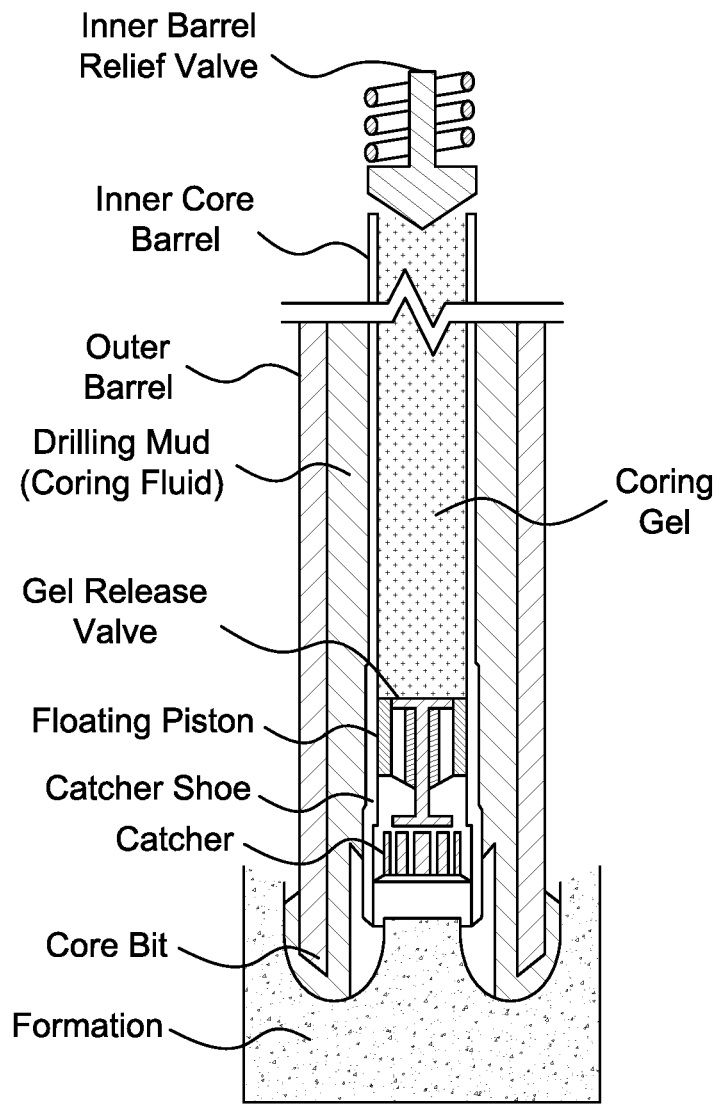
FIG. 16A: Extraction of the soft cores with the help of gel encapsulation system.
Figure 16B:
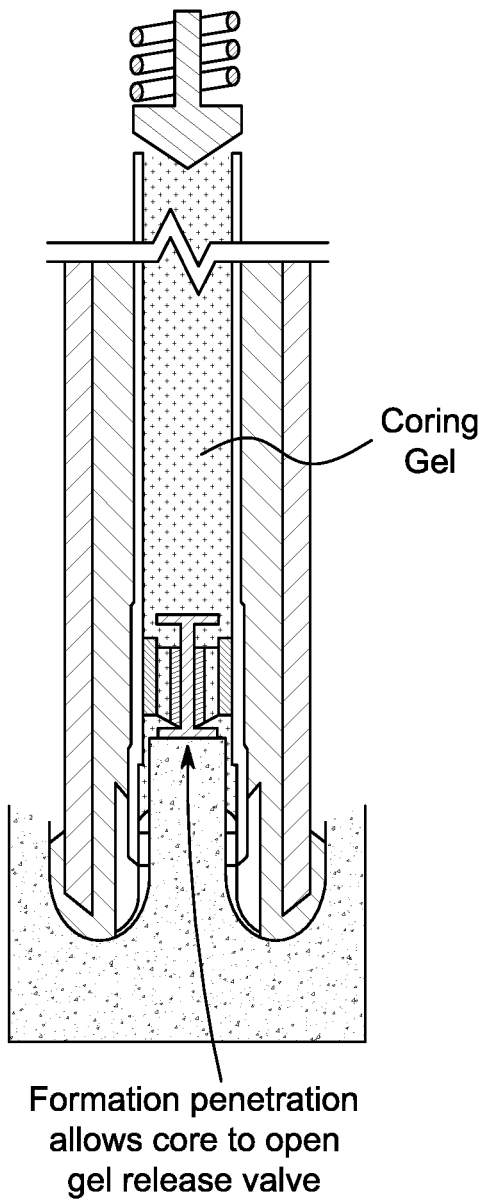
FIG. 16B: Extraction of the soft cores with the help of gel encapsulation system.
Figure 16C:
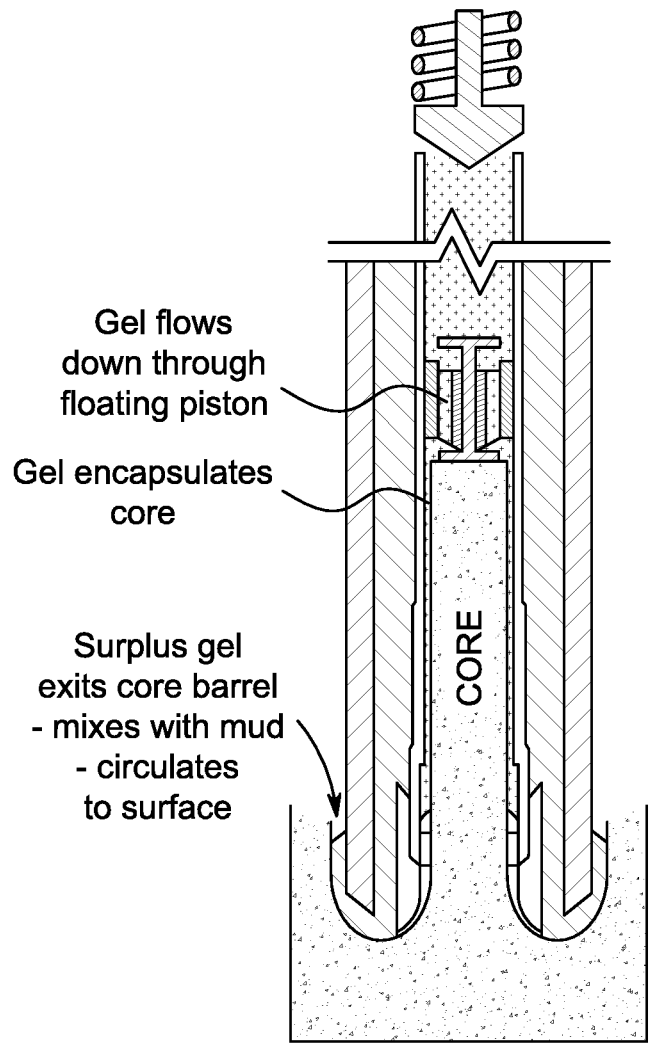
FIG. 16C: Extraction of the soft cores with the help of gel encapsulation system.

The embodiment of FIGS. 16A-C also addresses the extraction of softer cores that are easily fragmentable and would require coating and encapsulation in an extraction gel. In this embodiment, the rotation of the hard edge of the drilling bit penetrates the formation with the assistance of the drilling fluid, cooling the bit and carrying away the debris. The catcher is extended in the soft formation, sinking in and encompassing a cylindrical element. The catcher shoe engages the loaded catcher from the drill side, and the assembly is drawn in the drill by the floating piston. The movement of the catcher shoe inside the drill opens the protective gel valve, which exits and hardens, while the soft formation continues to be drawn in, with the encapsulating gel forming a hard skin preserving the structural integrity of the sample. With the parts of the core not coated by the gel, a sequence of the cores can be loaded in the permeameter 13 allowing hydraulic connection with the manometer entries through the uncoated rims on the core outer surface. In still another embodiment, the system of FIG. 17 may be provided without gel loading if the strength and aspect ratio of the extracted core allows.

Applications of the Measured Permeability Values

The concept of permeability is of importance to determining the flow characteristics of hydrocarbons in oil and gas reservoirs, and of groundwater in aquifers. For rock to be considered as an exploitable hydrocarbon reservoir without stimulation, its permeability must be greater than approximately 100 millidarcy (depending on the nature of the hydrocarbon—gas reservoirs with lower permeabilities are still exploitable because of the lower viscosity of gas with respect to oil). Rocks with permeabilities significantly lower than 100 md can form efficient seals. Unconsolidated sands may have permeabilities of over 5000 md. The concept also has many practical applications outside of geology, for example in chemical engineering (e.g., filtration), as well as in civil engineering when determining whether the ground conditions of a site are suitable for construction.

The broad term for the field where the hydraulic permeability data are utilized is access to the drinking water and drainage of the excess.

In the arid Middle East conditions, it is the availability of the aquifers and minimization of rain-water losses that make the present inventive method especially relevant. In the regions of South-East Asia, such as Vietnam, Cambodia or Thailand, the excessive flooding during winter creates a different burden on the economies and populations. In the United States, 51% of the drinking water comes from groundwater supplies. Around 99% of the rural population depends on groundwater. In addition, 64% of the total groundwater of the country is used for irrigation, and some of it is used for industrial processes and recharge for lakes and rivers. In 2010, 22 percent of freshwater used in USA came from groundwater and the other 78 percent came from surface water. Groundwater is important for some states that don't have access to fresh water. most of the fresh groundwater 65 percent is used for irrigation and the 21 percent is used for public purposes drinking mostly Correct values of permeability are important for the objective calculation of flow to drains or to a well field in an aquifer with the aim to control the water table. Other applications include subsurface drainage by pipes, tile drains or ditches. An alternative subsurface drainage method is drainage by wells. These calculations are essential for urban planning and agriculture, as well as for planning of water supply.

In one practically important embodiment, the experimentally measured values of permeability are incorporated in the MODFLOW computational package—and thus become usable and interchangeable in practical calculations by hydrology professionals. It is free software developed, documented and distributed by the USGS. MODFLOW is a modular finite-difference flow model, which is a computer code that solves the groundwater flow equation. The program is used by hydrogeologists to simulate the flow of groundwater through aquifers.

The software addresses at least the following practical problems without limiting: aquifer simulation; groundwater simulation and modeling; solute transport; variable-density flow; aquifer-system compaction; parameter estimation; groundwater management; unsaturated flow; seawater intrusion; aquatic biology and ecosystems; contaminant transport modeling; evapotranspiration; aquifers, wells, and springs; groundwater/surface-water interactions; karst, sinkholes, and land subsidence; lakes and reservoirs; physical habitats and environmental flows; pollution (chemical and biological).

The source code is free public domain software written primarily in Fortran and can compile and run on Microsoft Windows or Unix-like operating systems. Since its original development in the early 1980s, the USGS has made four major releases, and is now considered to be the de facto standard code for aquifer simulation. There are several actively developed commercial and non-commercial graphical user interfaces for MODFLOW. Many commercial products have grown up around it, providing graphical user interfaces to its input file-based interface, and typically incorporating pre- and post-processing of user data. Many other models have been developed to work with MODFLOW input and output, making linked models which simulate several hydrologic processes possible (flow and transport models, surface water and groundwater models and chemical reaction models), because of the simple, well-documented nature of MODFLOW. (See: McDonald M G, Harbaugh A W, original authors of MODFLOW. The history of MODFLOW. Groundwater. 2003 March; 41(2): 280-3; Harbaugh A W. MODFLOW-2005, the US Geological Survey modular ground-water model: the ground-water flow process. Reston, Va.: US Department of the Interior, US Geological Survey; 2005 Mar. 20; Kim N W, Chung I M, Won Y S, Arnold J G. Development and application of the integrated SWAT-MODFLOW model. Journal of hydrology. 2008 Jul. 1; 356(1-2):1-6; Prudic D E, Konikow L F, Banta E R. A new streamflow-routing (SFR1) package to simulate stream-aquifer interaction with MODFLOW-2000. 2004; Winston R B. ModelMuse: a graphical user interface for MODFLOW-2005 and PHAST. Reston, Va.: US Geological Survey; 2009; each incorporated herein by reference in its entirety).

The governing partial differential equation for a confined aquifer used in MODFLOW is:

$$\left(\frac{\partial}{\partial x}\right)\left[Kxx\frac{\partial h}{\partial x}\right] + \left(\frac{\partial}{\partial y}\right)\left[Kyy\frac{\partial h}{\partial y}\right] + \left(\frac{\partial}{\partial z}\right)\left[Kzz\frac{\partial h}{\partial z}\right] + W = Ss\left(\frac{\partial h}{\partial t}\right) \quad (20)$$

Kxx; K yy; Kzz—are respectively the values of hydraulic conductivity along the x, y, and z coordinate axes (m/sec);
h is the potentiometric head (m);
W—is a volumetric flux per unit volume representing sources and/or sinks of water, where negative values are extractions, and positive values are injections (m3/sec);
$S_s$—is the specific storage of the porous material ($L^{-1}$); and
t—is time (sec)

The equation (20) incorporates the permeability values in three independent dimensions, which can be measured by the inventive method. In most of cases Kxx≈Kyy (horizontal permeability), however Kzz is not equal generally.

Equation (20) does not have an analytical solution and needs to be solved numerically by the method of finite differences. The implementation of the algorithm involved dividing the zone of interest in volume grid consisting of small volume voxels. Each voxel is described by the equation (20) with the parameters (K, S) unchanging within the elementary volume. In its numerical form, the equation (20) is expanded to include the source, the sink and the changing head within a finite element, all combining into time-dependence dh/dt on the right side of (20). The sources for the given finite cell are the neighboring cells, the sinks are other neighboring cells, the pressure gradient is determined by the position, initial pressure distribution, hydraulic conductivities in all directions and the volume flow. In local zones combining several voxels of the 3D grid, the values in each cell are iteratively re-computed to observe convergence, and the next cell is included, extending the volume covered by the computation zone. The potential errors in such computations would propagate and accumulate with the number of the finite elements (voxels) included in the process.

One approach to minimize the program error is to apply boundary conditions when they are known, for example, the hydrostatic head on the surface is equal to zero, the flow in the zone is known, the outflow is equal to inflow. The converged computation must agree with these facts. The more experimental values are incorporated in the model, the lower the propagated error becomes. Such values are flows, specific storage and directional permeability values, all subject to the present inventive method. The numerical model should reproduce the experimental data in the aquifer locations where they were measured (or samples extracted). In case of discrepancy, the computational process can be iteratively updated to satisfy the boundary conditions. Especially valuable is the time-dependent and pressure-dependent grid of 3D values for anisotropic permeability.

Other non-limiting examples of modeling products, developed on the basis of MODFLOW and incorporating the customized permeability values produced by the inventive method are, without limitation:

SUTRA, a 2D or 3D density-dependent flow model by the USGS; Hydrus, a commercial unsaturated flow model; FEFLOW, a commercial modelling environment for subsurface flow, solute and heat transport processes; OpenGeoSys, a scientific open-source project for thermo-hydro-mechanical-chemical (THMC) processes in porous and fractured media; COMSOL Multiphysics (a commercial general modelling environment), FEATool Multiphysics an easy to use MATLAB simulation toolbox, and Integrated Water Flow Model (IWFM). Commercial MODFLOW programs are typically used by governments and consultants for practical applications of MODFLOW to real-world groundwater problems. Professional versions of MODFLOW are listed without limitation: Argus ONE; GMS—Groundwater Modeling System; Groundwater Vistas; Leapfrog Hydro; Processing Modflow; Visual MODFLOW.

Most of these products have a dialogue option where the software enquires about the parameters needed for entry by the customer. As an alternative, default solutions are available for each situation, but loss of quality is inevitable without the actual measured data. Thus, the present simple and rigorous method of determining multiple hydrological parameters is crucial for the improved performance of any among extensive hydrological modeling software available for the field.

Having generally described this disclosure, a further understanding can be obtained by reference to certain specific examples which are provided herein for purposes of illustration only and are not intended to be limiting unless otherwise specified.

Example 1: Computation of Hydraulic Transmissivity

Figure 17:
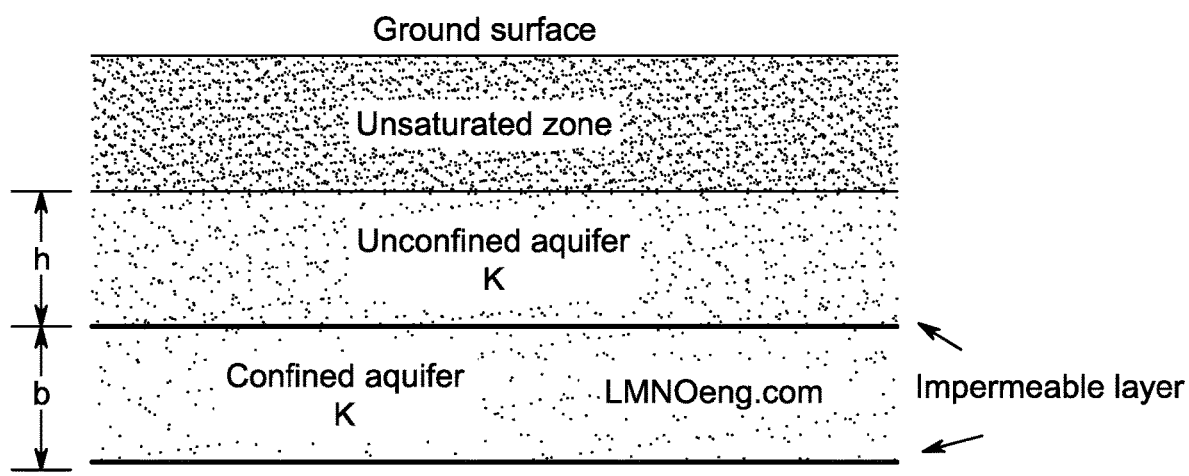
FIG. 17: Scheme for conducting groundwater transmissivity calculations.

Aquifer transmissivity is a useful parameter in groundwater flow modeling. Transmissivity includes the aquifer hydraulic conductivity which is a property of the aquifer. Hydraulic conductivity is a function of the fluid moving through the porous medium (i.e. aquifer, formation) and the permeability of the formation. In addition to hydraulic conductivity, transmissivity is a function of aquifer thickness (FIG. 17). In unconfined aquifers, the aquifer thickness is a height h, that is the water depth above an impermeable boundary. If a well is pumped, h can vary with time and location. In confined aquifers, the aquifer thickness b is independent of any effects of pumping since the aquifer is bound between two impermeable layers. The transmissivity values are:

$$Tb = Kb \quad (21)$$

$$Th = Kh \quad (22)$$

Where:
b=Confined aquifer thickness (m).
h=Height of water table in unconfined aquifer (m).
K=Aquifer hydraulic conductivity (m/s).
T=Aquifer transmissivity (m²/s).

From the transport perspective, equations (21) and (22) reflect water entering the table through the lateral sections proportional to b and h. But water propagates along the aquifer in proportion to K. Thus, the product of K by h or b indicates how much water can cross a section of an aquifer 1 m long in width in the direction from left to right (along the Earth's surface, tangentially). A wider aquifer (for example 10 km) with thickness b can carry more water than a narrower reference (1 km, thickness b), explaining the need to normalize to 1 m of width. Transmissivity is valuable in assessing how much water can be transported to an artesian well daily or how many draining wells are needed to absorb a typical and excessive rainfall in a city, while avoiding flooding. Permeability of the core extracted from the depth matching the groundwater table and measured by the inventive method provides this information, while the compression in the cell 13 models the geostatic pressure experienced by the layer at the depth b+h.

If the water layers are laminated, the total transmissivity is the sum of the products $K_i d_i$, where d is the thickness of a given layer and K its conductivity. When a soil layer is above the water table, it is not saturated and does not contribute to the transmissivity (lateral transfer of water elements is absent). When the soil layer is entirely below the water table, its saturated thickness corresponds to the thickness of the soil layer itself. When the water table is inside a soil layer, the saturated thickness corresponds to the distance of the water table to the bottom of the layer. As the water table may behave dynamically, this thickness may change from place to place or from time to time, so that the transmissivity may vary accordingly.

In a semi-confined aquifer, the water table is found within a soil layer with a negligibly small transmissivity, so that changes of the total transmissivity resulting from changes in the level of the water table are negligibly small (most of water movement is vertical, not lateral). When pumping water from an unconfined aquifer, where the water table is inside a soil layer with a significant transmissivity, the water table may be drawn down whereby the transmissivity reduces and the flow of water to the well diminishes.

Example 2: Computation of Hydraulic Resistance

Vertical water transfer is equally important to the lateral. The resistance to vertical flow of an individual soil layer with a saturated thickness $d_i$ and vertical hydraulic conductivity $K_{iv}$ is:

$$Ri = di/Kiv \quad (23)$$

The resistances combine for the subsequent layers, and the apparent vertical conductivity of the aquifer is:

$$Kva = Dt/(\Sigma di/Ki) \quad (24)$$

Where Dt is the total thickness of the aquifer.

The vertical conductivity of the total is limited by the resistances of poorly permeable layers.

The values of vertical permeability find application, according to (24) in the calculation of the amount of water that can be absorbed by the soil in the aquifer and later transferred away by the lateral transmissivity mechanism, leak outside of the aquifer or diffuse back to the surface and evaporate. Complete saturation of an aquifer means that there is an uninterrupted column of water level reaching the surface and the hydrostatic pressure of this column balances the hydrostatic potential of each new element that is present on a saturated area of soil and is the driving force for the absorption of the surface water in the ground. These complex relationships are implied in the value of K for the given element of soil surface. The complex interplays between lateral and vertical hydraulic conductivity determine overall movement of water masses under the ground (flow-nets).

Example 3: Computation of Aquifer Capacity

Storativity or the storage coefficient is the volume of water released from storage per unit decline in hydraulic head in the aquifer, per unit area of the aquifer. Storativity is a dimensionless quantity and is always greater than 0.

$$S = \left(\frac{dVw}{dh}\right)\left(\frac{1}{A}\right) = Ssb + Sy \quad (25)$$

Where S is storativity;
Vw—is the volume of water released from storage ([m³]);
h—is the hydraulic head ([m]); Ss—is the specific storage; Sy—is the specific yield; b is the thickness of aquifer; A is the area ([m²]).

The specific storage multiplied by the thickness of the confined component of the aquifer produces the Ss b components, while the contribution of the unconfined layers is Sy. The equation (25) can be understood thus: the more capacity is in the layer, the less its intensive parameter (h or hydrostatic head) is impacted by withdrawing a fixed mass of water (for example in a neighboring well).

The inventive apparatus is applicable for measuring storativity, which in turn describes the capacity of the aquifer determining the scope of its use. Storativity is the essential parameter of the governing groundwater equation (20) used by MODFLOW and similar software tools of aquifer analysis. In terms of measurable physical properties, specific storage can be expressed as:

$$Ss = \gamma w(\beta p + n\beta w) \quad (26)$$

Where $\gamma_w$—is the specific weight of water (N/m3); $\beta_p$—is the compressibility of the main aquifer material (m²/N⁻¹); $\beta_w$—is the compressibility of water (m²/N⁻¹); n is the porosity of the material (dimensionless).

Figure 8:
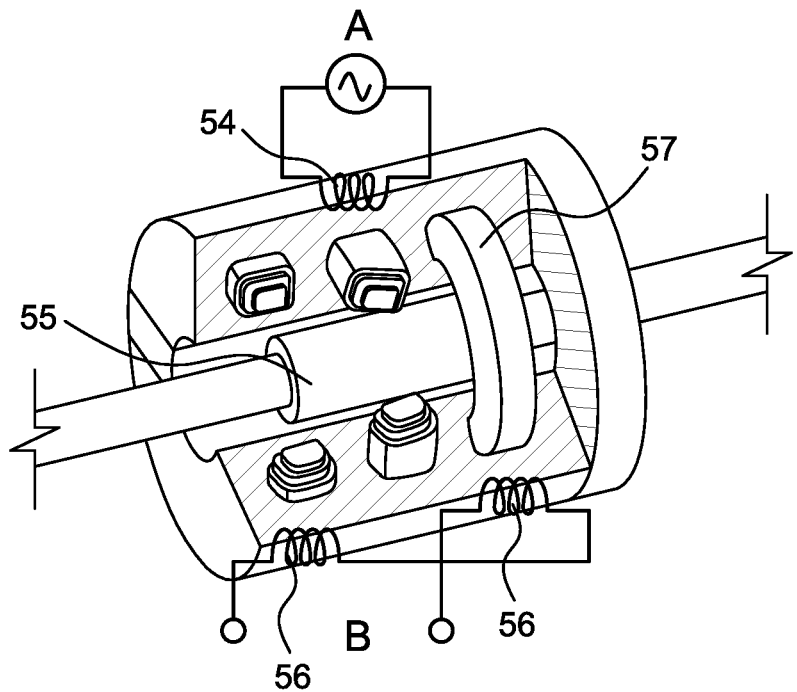
FIG. 8: Linear Variable Differential Transformer sensor of deformations.

All parameters required for the computation of (26) are available using the embodiment of FIG. 8. The stress value, deformation value, resulting porosity, the initial porosity, compressibility of water, compressibility of soil can be measured in the inventive system.

Example 4: Use of the Device for Permeability Anisotropy Determination

When horizontal and vertical hydraulic conductivity of a soil layer differ considerably, the layer is said to be anisotropic with respect to hydraulic conductivity. An aquifer is called semi-confined when a saturated layer with a relatively small horizontal hydraulic conductivity (the semi-confining layer or aquitard) overlies a layer with a relatively high horizontal hydraulic conductivity so that the flow of groundwater in the first layer is mainly vertical and in the second layer mainly horizontal. The resistance of a semi-confining top layer of an aquifer can be determined from pumping tests or from the laboratory studies by the inventive apparatus. When calculating flow to drains or to a well field in an aquifer with the aim to control the water table, the anisotropy has to be taken into account to avoid misleading results.

The inventive device and method are suitable for computing anisotropy by extracting 2 cores in the different directions. One core is extracted from a vertically drilled well that reached the aquifer. The second well direction is slanted, forming the angle θ with the vertical. Both angles of extraction are recorded, and the samples are analyzed in the inventive apparatus, producing the value of $K_v$ (vertical) and $K_m$ (mixed). The horizontal component can be computed from the mixed permeability by the formula:

$$Km2 = Kv2 \cos 2\theta + Kh2 \sin 2\theta \quad (27)$$

Where Kv and Kh are the vertical and horizontal permeabilities, respectively.

With the permeability different in the directions x and y of the horizontal plane, two slanted wells are required—one slanted along the North-South direction (axis x) and another slanted along the East-West direction (axis y). The Kxx, Kyy and Kzz of the groundwater transport equation (20) can be identified from the equations:

$$Kxz2 = Kzz2 \cos 2\theta xz + Kxx2 \sin 2\theta xz \quad (28);$$

$$Kyz2 = Kzz2 \cos 2\theta yz + Kyy2 \sin 2\theta yz \quad (29).$$

Where:
Kzz—is the permeability measured using the vertically extracted core;
Kxz, Kyz—are the permeabilities measured using the cores extracted from the slanted wells in the respective directions;
Kxx, Kyy—are the unknown horizontal permeabilities in the North-South and East-West directions;
θxz is the angle between the slanted North-South well direction and vertical axis z;
θyz is the angle between the slanted East-West well direction and vertical axis z;

Example 5: Calibration of the Research Methodology by an In-Situ Aquifer Test Using the Theis Equation An aquifer test (or a pumping test) is conducted to evaluate an aquifer by "stimulating" the aquifer through constant pumping and observing the aquifer's "response" (drawdown) in observation wells. Aquifer testing is a common tool that hydrogeologists use to characterize a system of aquifers, aquitards and flow system boundaries. Aquifer tests are typically interpreted by using an analytical model of aquifer flow (the most fundamental being the Theis solution) to match the data observed in the real world, then assuming that the parameters from the idealized model apply to the real-world aquifer. Aquifer testing utilizes one or more monitoring wells, or piezometers ("point" observation wells). A monitoring well is a well which is not being pumped (but is used to monitor the hydraulic head in the aquifer). Typically, monitoring and pumping wells are screened across the same aquifers. Most commonly an aquifer test is conducted by pumping water from one well at a steady rate and for at least one day, while carefully measuring the water levels in the monitoring wells. When water is pumped from the pumping well the pressure in the aquifer that feeds that well declines. This decline in pressure shows up as a drawdown (change in the hydraulic head) in an observation well. Drawdown decreases with radial distance from the pumping well and drawdown increases with the length of time that the pumping continues.

The aquifer characteristics which are evaluated by most aquifer tests are: Hydraulic conductivity: the rate of flow of water through a unit cross-sectional area of an aquifer, at a unit hydraulic gradient (m³ per day per m²). Units are frequently shortened to meters per day or equivalent. Specific storage or storativity: a measure of the amount of water a confined aquifer yields for a certain change in head. Transmissivity: the rate at which water is transmitted through whole thickness and unit width of an aquifer under a unit hydraulic gradient. It is equal to the hydraulic conductivity times the thickness of an aquifer. Additional aquifer characteristics which are sometimes evaluated, depending on the type of aquifer, include: specific yield or drainable porosity: a measure of the amount of water an unconfined aquifer yields when completely drained; leakage coefficient: some aquifers are bounded by aquitards which slowly give up water to the aquifer, providing additional water to reduce drawdown; the presence of aquifer boundaries (recharge or no-flow) and their distance from the pumped well and piezometers.

The well-testing data link up with the permeameter data through the Theis equation(s):

$$s = \left(\frac{Q}{4\pi T}\right) W(u) \quad (30)$$

$$u = r2S/4Tt \quad (31)$$

where s is the drawdown (change in the hydraulic head at a point since the beginning of the test), u is a dimensionless time parameter, Q is the discharge (pumping) rate of the well (volume divided by time, or m³/s), T and S are the transmissivity and storativity of the aquifer around the well (m²/s and unitless, respectively), r is the distance from the pumping well to the point where the drawdown was observed (m), t is the time since pumping began (seconds), and W(u) is the "Well function" (called the exponential integral, E1, in non-hydrogeology literature).

The well function is approximated by the infinite series:

$$W(u) = -0.577216 - \ln(U) + U - \frac{U2}{2x2!} + \frac{U3}{3x3!} - \frac{U4}{4x4!} \quad (32)$$

Typically, this equation is used to find the average T and S values near a pumping well, from drawdown data collected during an aquifer test.

Knowing the dimensions of the aquifer allows to translate the transmissivity values into hydraulic conductivity and to compare the storativity found through the compressive permeameter study (Example 3) with the storativity that follows the fit of the well test data to the Theis equation.

Comparisons of the in-situ results with the laboratory measurements by the inventive method allow calibration of the laboratory results, especially for the same locality and formation. Each measurement receives empirical corrections that minimize the discrepancies between the numbers predicted from the preliminary drilling and lab testing, followed by MODFLOW predictions (low-cost analysis) and real in-situ aquifer tests described above (high-cost analysis). The inventive method allows, after calibration, to reduce the scope of the high-cost component (testing well drilling) by increased low-cost sampling (a few wells, with the results joined by running MODFLOW or similar numerical tools).

Example 6: Calibration of the Research Methodology by an In-Situ Aquifer Test Using the Thiem Solution In a confined aquifer a steady-state approximation may lead to acceptable precision of results.

If the cone of hydrostatic head depression surrounding a pumping well is stabilized (i.e. drawdown and radius of influence are static) the Thies equation is used to determine the hydraulic conductivity for the aquifer (note: the storage coefficient cannot be found under steady-state conditions). For an unconfined aquifer with two observation wells:

$$K = Q\log\left(\frac{r2}{r1}\right) / [1.366(h22 - h12)] \quad (33)$$

Where:
$r_1$—is the distance to the nearest observation well;
$r_2$—is the distance to the farthest observation well;
$h_x$—is the saturated thickness at the given observation well;
Q—is the pumping rate.

This equation adapted for confined aquifers is:

$$K = Q\log\left(\frac{r2}{r1}\right) / [2.73\ b\ (h2 - h1)] \quad (34)$$

$$T = Q\log\left(\frac{r2}{r1}\right) / [2.73(s2 - s1)] \quad (35)$$

where:
b—is the thickness of aquifer;
$h_{1,2}$—is the head in the observation well;
$s_{1,2}$—is the drawdown in the observation well;

The transmissivity of permeability of an aquifer can be directly obtained from equations (34) and (35).

The measurements can be aligned with the laboratory tests of the invention and become a source of calibrating corrections, with the motivation as in Example 5.

Example 7: Safety Aspects

Permeability is one of the important physical properties of soil as some of the major problems of soil mechanics are directly connected with it. Design of highways, airports, earth dams, construction of foundation below water—table, yield from a well, settlement of foundation etc. depend upon the permeability of soil. A material is said to be permeable if it contains continuous voids. Since such voids are contained in all soils including the stiffest clay, all these are permeable. Gravels are highly permeable, and stiff clay is the least permeable soil The knowledge of permeability is important for the following engineering problems:
(i) Seepage through earthen dams and canals.
(ii) Unfit pressure under hydraulic structure and safety against piping
(iii) Rate of settlement of a saturated com-pressable soil layer.
(iv) Yield from a well and drainage of water-logged agricultural land.
(v) Stability of upstream and downstream slopes of dams.

The observed permeabilities differ in a dramatically broad range:

TABLE 1

List of hydraulic permeabilities for the typical soils and construction materials:

| Formation | MIN (m/sec) | MAX (m/sec) |
|---|---|---|
| Fine Sand | 2.00E−07 | 2.00E−04 |
| Medium Sand | 9.00E−07 | 5.00E−04 |
| Coarse Sand | 9.00E−07 | 6.00E−03 |
| Sand; Clean; Good Aquifer | 1.00E−05 | 1.00E−02 |
| Sand/Gravelly Sand; Poorly Graded; Little to No Fines | 2.55E−05 | 5.35E−04 |
| Sand/Gravelly Sand; Well Graded; Little to No Fines | 1.00E−08 | 1.00E−06 |
| Inorganic Silty Fine Sand/Clayey Fine Sand; Slight Plasticity | 5.00E−09 | 1.00E−06 |
| Silty Sand | 1.00E−08 | 5.00E−06 |
| Clayey Sand | 5.50E−09 | 5.50E−06 |
| Alluvial Gravel/sand | 4.00E−04 | 4.00E−03 |

TABLE 1-continued

List of hydraulic permeabilities for
the typical soils and construction materials:

| Formation | MIN (m/sec) | MAX (m/sec) |
|---|---|---|
| Sand/Gravel; Uniform | 4.00E−03 | 4.00E−01 |
| Sand/Gravel; Well Graded; No fines | 4.00E−05 | 4.00E−03 |
| Gravel | 3.00E−04 | 3.00E−02 |
| Gravel/Sandy Gravel; Well Graded; Little to No Fines | 5.00E−04 | 5.00E−02 |
| Gravel/Sandy Gravel; Poorly Graded; Little to No Fines | 5.00E−04 | 5.00E−02 |
| Silty Gravel/Silty Sandy Gravel | 5.00E−08 | 5.00E−06 |
| Clayey Gravel/Clayey Sandy Gravel | 5.00E−09 | 5.00E−06 |
| Inorganic Silt; High Plasticity | 1.00E−10 | 5.00E−08 |
| Silt; Compacted | 7.00E−10 | 7.00E−08 |
| Inorganic Clay/Silty Clay/Sandy Clay; Low Plasticity | 5.00E−10 | 5.00E−08 |
| Organic Clay/Silty Clay; Low Plasticity | 5.00E−09 | 1.00E−07 |
| Marine Clay; Unweathered | 8.00E−13 | 2.00E−09 |
| Organic Clay; High Plasticity | 5.00E−10 | 1.00E−07 |
| Inorganic Clay; High Plasticity | 1.00E−10 | 1.00E−07 |
| Clay | 1.00E−11 | 4.70E−09 |
| Clay; Compacted | 1.00E−10 | 1.00E−09 |
| Limestone/Dolomite | 1.00E−09 | 6.00E−06 |
| Sandstone | 3.00E−10 | 6.00E−06 |
| Siltstone | 1.00E−11 | 1.40E−08 |
| Anhydrite | 4.00E−13 | 2.00E−08 |
| Shale | 1.00E−13 | 2.00E−09 |
| Permeable Basalt | 4.00E−07 | 2.00E−02 |
| Igneous/Metamorphic Rock; Fractured | 8.00E−09 | 3.00E−04 |
| Granite; Weathered | 3.30E−06 | 5.20E−05 |
| Gabbro; Weathered | 5.50E−07 | 3.80E−06 |
| Basalt | 2.00E−11 | 4.20E−07 |
| Igneous/Metamorphic Rock; Unfractured | 3.00E−14 | 2.00E−10 |

With many aspects impacting safety directly (flooding, accidents, sanitation, transport, contamination) and indirectly (feasibility of agriculture, construction), it is important to note a remarkably broad range of permeability even in the same types of formations. The MODFLOW and derived software products are based on numerical iteratively convergent processes that depend on the boundary conditions for the agreement with reality. In the absence of empirical feedback and customer-supplied data, the predictions by the tool alone are inadequate. There is a little alternative to testing—either in-situ or under the laboratory conditions. The laboratory testing process of the invention is very versatile, allowing to derive both constant and time-dependent permeability functions without the need to solve the groundwater equation. This versatility is achieved by the key feature of the apparatus—multiple manometers vertically stacked on one side of the wall. Under each applied pressure, the resulting permeability can be constant, profiled, have a finite asymptotic level, have a zero asymptotic level. This time dependence is especially useful for the analysis of safety-related and time-dependent events with a shorter timescale, comparable to the timescale of the laboratory tests. The group of events especially suitable to the analysis by the inventive device are: flooding, rainfalls, stimulated oil and gas recovery, transient and unstable aquifers in the arid climates, irrigation by scarce water resources in the arid climates.

The invention claimed is:

1. A hydraulic confinement and measuring system for determining hydraulic conductivity of porous carbonates and sandstones, comprising:
a cylindrical pressurized cell configured to contain a porous material selected from the group consisting of a carbonate and a sandstone and having an entry line and an exit line for ingress and egress of a water flow;
wherein the entry line enters at a lowest sidewall position or bottom of the apparatus, and the exit line exists at a highest sidewall position or through a closing lid of the cylindrical pressurized cell;
wherein the cylindrical pressurized cell is provided with from 3 to 30 tube manometers attached in a stacked manner one above the other on the same sidewall of the cylindrical pressurized cell, the said manometers being separated by equal intervals;
wherein the cylindrical pressurized cell is provided with a compressor connected to a ram configured to exert a vertical pressure on the porous material;
a plurality of synchronized detectors configured to measure an entering volume flow, an exiting volume flow, levels of water in the tube manometers, a vertical compression and/or a lateral compression and a mechanical deformation of the porous material; and
a base plate on which the cylindrical pressurized cell and a linear variable differential transformer (LVDT) are mounted; wherein the LVDT is connected to the ram;
wherein the synchronized detectors are integrated and synchronized by a computerized controller having computer instructions to calculate a hydraulic conductivity of the porous material based on measurements from the plurality of synchronized detectors.

2. The apparatus of claim 1, comprising a digital video-camera configured to simultaneously detect the levels of the tube manometers.

3. The apparatus of claim 1, further comprising a tank connected to the entry line configured to provide a constant head level disposed above the pressurized cylindrical cell.

4. The apparatus of claim 3, wherein the entering line is pressurized by a falling head level in the tank disposed above the pressurized cylindrical cell.

5. The apparatus of claim 1, wherein the entry line and the exit line transmit a fluid at known temperatures, and the temperatures are synchronized with the other sensors.

6. The apparatus of claim 1, comprising LVDT sensors configured to measure the mechanical deformation of the porous sample.

* * * * *